United States Patent
Phan

(10) Patent No.: US 8,021,365 B2
(45) Date of Patent: Sep. 20, 2011

(54) SURGICAL DEVICE HAVING INTERCHANGEABLE COMPONENTS AND METHODS OF USE

(75) Inventor: Christopher U. Phan, San Leandro, CA (US)

(73) Assignee: Kyphon SARL, Neuchatel (CH)

( * ) Notice: Subject to any disclaimer, the term of this patent is extended or adjusted under 35 U.S.C. 154(b) by 1199 days.

(21) Appl. No.: 11/731,364

(22) Filed: Mar. 30, 2007

(65) Prior Publication Data

US 2007/0260257 A1 Nov. 8, 2007

Related U.S. Application Data

(63) Continuation-in-part of application No. PCT/US2006/026526, filed on Jul. 10, 2006, which is a continuation-in-part of application No. 11/256,036, filed on Oct. 21, 2005.

(60) Provisional application No. 60/698,288, filed on Jul. 11, 2005.

(51) Int. Cl.
*A61B 17/00* (2006.01)
(52) U.S. Cl. .......................................... 606/85
(58) Field of Classification Search .................... 606/84, 606/85
See application file for complete search history.

(56) References Cited

U.S. PATENT DOCUMENTS

| 3,852,884 | A | 12/1974 | Lazarus |
| 4,083,369 | A | 4/1978 | Sinnreich |
| 4,313,434 | A | 2/1982 | Segal |
| 4,327,736 | A | 5/1982 | Inoue |
| 4,429,691 | A | 2/1984 | Niwa et al. |
| 4,720,264 | A | 1/1988 | Lazarus |
| 4,904,257 | A | 2/1990 | Mori et al. |
| 4,969,888 | A | 11/1990 | Scholten et al. |
| 5,108,404 | A | 4/1992 | Scholten et al. |
| 5,163,949 | A | 11/1992 | Bonutti |
| 5,254,091 | A | 10/1993 | Aliahmad |
| 5,331,975 | A | 7/1994 | Bonutti |

(Continued)

FOREIGN PATENT DOCUMENTS

CN 87210489 6/1988

(Continued)

OTHER PUBLICATIONS

International Search Report in PCT/US2008/003561, filed Mar. 19, 2008, 7 pages.

(Continued)

*Primary Examiner* — Eduardo C Robert
*Assistant Examiner* — Elana B Fisher
(74) *Attorney, Agent, or Firm* — Haynes and Boone, LLP

(57) ABSTRACT

A surgical device, kit, and/or method for interchanging components of the surgical device can include a handle, a docking assembly, a shaft assembly, a coupler assembly, and a surgical implement. The handle can have a lever pivotably connected to the handle, and the docking assembly secured to the handle. The docking assembly can include a docking rod operably attached to the lever and axially slidable within the docking assembly. The shaft assembly can include a shaft rod axially slidable within a detachable shaft and removably attachable to the docking rod. The coupler assembly can be adapted to releasably secure the shaft assembly to the docking assembly. The surgical implement can be attached to a distal end of the shaft rod operable with the lever. The shaft assembly and surgical implement may be interchanged on the handle with other shaft assemblies and surgical implements.

9 Claims, 20 Drawing Sheets

U.S. PATENT DOCUMENTS

| | | |
|---|---|---|
| 5,337,638 A | 8/1994 | Coss et al. |
| 5,366,412 A | 11/1994 | Beaty et al. |
| 5,439,447 A | 8/1995 | Miraki |
| 5,562,699 A | 10/1996 | Heimberger et al. |
| 5,667,520 A | 9/1997 | Bonutti |
| 5,685,826 A | 11/1997 | Bonutti |
| 5,707,390 A | 1/1998 | Bonutti |
| 5,716,325 A | 2/1998 | Bonutti |
| 5,782,834 A | 7/1998 | Lucey et al. |
| 5,972,015 A | 10/1999 | Scribner et al. |
| 6,042,596 A | 3/2000 | Bonutti |
| 6,048,346 A | 4/2000 | Reiley et al. |
| 6,066,154 A | 5/2000 | Reiley et al. |
| 6,132,435 A | 10/2000 | Young |
| 6,162,053 A | 12/2000 | Hollander |
| 6,187,000 B1 | 2/2001 | Davison et al. |
| 6,201,978 B1 | 3/2001 | Buschmann |
| D439,980 S | 4/2001 | Reiley et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,280,456 B1 | 8/2001 | Scribner et al. |
| D449,691 S | 10/2001 | Reiley et al. |
| 6,423,083 B2 | 7/2002 | Reiley et al. |
| 6,425,859 B1 | 7/2002 | Foley et al. |
| 6,440,138 B1 | 8/2002 | Reiley et al. |
| 6,468,279 B1 | 10/2002 | Reo |
| D467,657 S | 12/2002 | Scribner |
| D469,871 S | 2/2003 | Sand |
| 6,575,919 B1 | 6/2003 | Reiley et al. |
| 6,579,532 B1 | 6/2003 | Mandel et al. |
| 6,607,544 B1 | 8/2003 | Boucher et al. |
| 6,613,054 B2 | 9/2003 | Scribner et al. |
| 6,620,181 B1 | 9/2003 | Bonutti |
| 6,623,505 B2 | 9/2003 | Scribner et al. |
| 6,632,235 B2 | 10/2003 | Weikel et al. |
| D482,787 S | 11/2003 | Reiss |
| 6,641,587 B2 | 11/2003 | Scribner et al. |
| 6,645,213 B2 | 11/2003 | Sand et al. |
| D483,495 S | 12/2003 | Sand |
| 6,663,647 B2 | 12/2003 | Reiley et al. |
| 6,679,886 B2 | 1/2004 | Weikel et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,740,093 B2 | 5/2004 | Hochschuler et al. |
| 6,800,084 B2 | 10/2004 | Davison et al. |
| 6,814,736 B2 | 11/2004 | Reiley et al. |
| 6,887,246 B2 | 5/2005 | Bhatnagar et al. |
| 2002/0022856 A1 | 2/2002 | Johnson et al. |
| 2002/0026195 A1 | 2/2002 | Layne et al. |
| 2002/0032447 A1 | 3/2002 | Weikel et al. |
| 2002/0058947 A1 | 5/2002 | Hochschuler et al. |
| 2002/0099384 A1 | 7/2002 | Scribner et al. |
| 2002/0161373 A1 | 10/2002 | Osorio et al. |
| 2002/0177866 A1 | 11/2002 | Weikel et al. |
| 2003/0004530 A1* | 1/2003 | Reo ............................. 606/185 |
| 2003/0032963 A1 | 2/2003 | Reiss et al. |
| 2003/0050644 A1 | 3/2003 | Boucher et al. |
| 2003/0191414 A1 | 10/2003 | Reiley et al. |
| 2004/0010260 A1 | 1/2004 | Scribner et al. |
| 2004/0049203 A1 | 3/2004 | Scribner et al. |
| 2004/0133208 A1 | 7/2004 | Weikel et al. |
| 2004/0133280 A1 | 7/2004 | Trieu |
| 2004/0210297 A1 | 10/2004 | Lin et al. |
| 2004/0215344 A1 | 10/2004 | Hochschuler et al. |
| 2004/0225296 A1 | 11/2004 | Reiss et al. |
| 2005/0090862 A1 | 4/2005 | McDevitt et al. |
| 2005/0124999 A1 | 6/2005 | Teitelbaum et al. |
| 2006/0058791 A1 | 3/2006 | Broman et al. |
| 2006/0058884 A1 | 3/2006 | Aram et al. |
| 2006/0116689 A1 | 6/2006 | Albans et al. |
| 2006/0116766 A1 | 6/2006 | Lemaire |
| 2006/0122614 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |
| 2006/0122704 A1 | 6/2006 | Vresilovic et al. |
| 2006/0149379 A1 | 7/2006 | Kuslich et al. |
| 2006/0184192 A1 | 8/2006 | Markworth et al. |
| 2008/0009877 A1* | 1/2008 | Sankaran et al. ............... 606/84 |

FOREIGN PATENT DOCUMENTS

| | | |
|---|---|---|
| DE | 3709824 A1 | 10/1988 |
| EP | 0571057 | 11/1993 |
| EP | 0571057 A | 11/1993 |
| EP | 0908152 | 4/1999 |
| EP | 0908152 A | 4/1999 |
| JP | 8038618 | 2/1996 |
| WO | 9856301 | 12/1998 |
| WO | WO 98/56301 | 12/1998 |
| WO | WO 00/44319 | 8/2000 |
| WO | 2005023493 A2 | 3/2005 |
| WO | WO 2005/023085 | 3/2005 |
| WO | WO 2005/027726 | 3/2005 |
| WO | 2005032397 A1 | 4/2005 |
| WO | WO 2005/030318 | 4/2005 |

OTHER PUBLICATIONS

Bhan, S. et al., "Percutaneous Bone Grafting for Nonunion and Delayed Union of Fractures of the Tibial Shaft," International Orthopaedics (SICOT), vol. 17, pp. 310-312, 1993.

KyphX Express System, Reducing the Profile. Increasing your Options. 6 pages.

KyphX® Bone Filler Device, web page at http://www1.kyphon.com/professionals/prod_KyphX_BFD.cfm, as available via the Internet and printed Jul. 6, 2005.

Orthopedic Devices; Classification for the Resorbable Calcium Salt Bone Filler Device, Food and Drug Administration, Rules and Regulations, Federal Register, vol. 68, No. 105, 2003.

Liu et al., Treatment Planning and Verification of HDR Brachytherapy Using C-am Fluoroscopy, Department of Radiation Oncology, SUNY Upstate Medical University, Syracuse, New York.

METRx X™-Tube Retraction System-Innovative Design, web page at http://www.spineuniverse.com/displayarticle.php/article2146.html, as printed on Jul. 5, 2005.

METRx™ System: Introduction, web page at http://www.spineuniverse.com/displayarticle.php/article748.html, as printed on Jul. 5, 2005.

METRx™: Mimimal Access . . . : patient info-SofamorDanek.com, web page at http://www.sofamordanek.com/patient-minimal-metrx.html, as printed on Nov. 21, 2005.

International Search Report in PCT/US2006/026526, mailing date Feb. 20, 2007, 10 pages.

International Search Report in PCT/US2008/003561, filed Mar. 19, 2008, 7 pages.

* cited by examiner

SURGICAL DEVICE HAVING INTERCHANGEABLE COMPONENTS AND METHODS OF USE

CROSS REFERENCE TO RELATED APPLICATIONS

This application is a Continuation-in-Part application of, and claims benefit of, International Patent App. No. PCT/US2006/026526, filed on Jul. 10, 2006, which is a Continuation-in-Part application of, and claims benefit of, U.S. patent application Ser. No. 11/256,036, filed on Oct. 21, 2005, which claims benefit of U.S. Provisional Patent App. No. 60/698,288, filed on Jul. 11, 2005, each of which is incorporated by reference herein in its entirety. This application has a specification related to a U.S. patent application entitled "Torque Limiting Device and Methods" and a U.S. patent application entitled "Axial Load Limiting System and Methods," each filed on Mar. 30, 2007, each of which is incorporated by reference herein in its entirety.

FIELD OF THE INVENTION

The present invention relates to a surgical device having interchangeable components, kits comprising a surgical device having interchangeable components, and methods for using a surgical device having interchangeable components.

BACKGROUND

During the course of a surgical procedure, a surgical tool may undergo relatively high mechanical loads on various parts of the tool. Such mechanical loads may be rotational torque loads and/or axial loads. A tool having a surgical implement on one end that is inserted in a surgical site may require high torque forces in order to rotate the implement against hard tissue. If a torque force required to rotate the surgical implement is greater than the tool can withstand, the tool may be damaged and/or become inoperable. This may require the tool operator to remove the tool from the surgical site in order to repair the tool or to retrieve a replacement tool to continue with the procedure. Moreover, if a surgical tool is damaged or breaks while inserted in a patient, the patient may be injured.

Some conventional surgical tools have been designed to break in a predetermined position when torque forces greater than the tool can withstand are applied. For example, a tool may include a groove at a particular location such that a predetermined torque causes the tool to break at the groove. The predetermined torque breaking point may require less torque force to break that portion of the tool than would cause other portions of the tool to break. In this way, the tool may break prior to breakage in a more undesirable portion of the tool that may cause injury to a patient.

A disadvantage of such a conventional design is that when the tool breaks, the surgeon must stop the procedure to repair or replace the tool. Another disadvantage is that once the tool breaks, it may be un-repairable and thus require replacement, which can be costly.

A tool having a surgical implement on one end that is inserted in a surgical site may require high axial forces in order to manipulate the implement in certain environments. In a surgical device having a handle and a lever system, a significant axial load can be generated on the connections and attachments of the device. For example, when a curette tip attached to the distal end of a surgical device shaft is inserted into hard bone, articulation of the curette tip about a pivot point to an angle away from the shaft of the device can be restricted by the bone. As increasing axial load is placed on the device, the axial load can exceed the strength of the connection of the curette tip to the device and/or the pivot point. As a result, the surgical curette device can become non-functional and/or damaged. In addition, in surgical sites comprising hard tissue, the curette tip may be able to be moved away from the shaft only in small increments. Such a process may involve repeated stopping of the procedure, such as bone scraping, in order to readjust the position of the lever relative to the handle to change the axial pressure and correspondingly the angle of the curette tip relative to the axis of the shaft.

Thus, it is desirable to provide a surgical device that avoids being damaged and/or becoming inoperable during use, particularly due to high torque and/or axial loads placed on the device.

Conventional surgical devices often have undetachable components, which are thus not interchangeable. For example, a surgical tool such as a curette can be configured with one shaft and curette assembled to a handle and cannot be detached. Some surgical procedures may require manipulation of a surgical implement such as a curette attached to the end of a shaft at various locations within a surgical site. For this purpose, the length, flexibility, or other characteristics of the shaft may need to be different for accessing different levels of the surgical site. In some procedures, different sizes, shapes, or other characteristics of the curette tip may be desired for scraping different tissues. Conventional surgical devices with undetachable components require the surgeon to use entirely separate multiple devices to have such procedural flexibility. Providing entirely separate multiple surgical tools for a single surgical procedure can be costly. Thus, it may be desirable to provide a surgical device having interchangeable components.

SUMMARY OF THE INVENTION

Some embodiments of the present invention can include a torque limiting device and/or system, tools, including surgical tools, comprising a torque limiting device, kits comprising a torque limiting device, and/or methods for using a torque limiting device.

In an illustrative embodiment, a surgical device can include a rod attached on one end to a rotatable handle and attached on the opposite end to a surgical implement, for example, a curette. A first torque limiting element can be connected to the handle. A second torque limiting element can be operably connected to the rod and surgical implement and releasably engageable with the first torque limiting element. When the first and second torque limiting elements are engaged, rotation of the handle can cause rotation of the rod and surgical implement. When a rotational force that exceeds a predetermined torque limit is applied to the handle, the first and second torque limiting elements can disengage from each other, so that the handle is rotatable without rotation of the rod and surgical implement. After becoming disengaged, the first and second torque limiting elements may be re-engaged so that further rotation of the handle can cause rotation of the rod and surgical implement. In this manner, an embodiment of the surgical device can be protected from damage and/or inoperability related to application of an excessive rotational torque to the device. In addition, an embodiment of the device may be re-engaged for further rotation of the surgical implement without removing the device from a surgical site.

In an embodiment, the first torque limiting element can comprise a first substantially planar surface, and the second torque limiting element can comprise a second substantially planar surface. The first and second planar surfaces can be biased against each other, for example, with a spring, such that, within a predetermined torque range, rotation of the first planar surface can cause rotation of the second planar surface in the same direction through frictional engagement of the surfaces. The first and second planar surfaces can be releasably engageable with each other. When a predetermined torque limit is surpassed, the two surfaces can become disengaged such that the first planar surface can rotate independently of the second planar surface. By decreasing the rotational force applied to the first planar surface, the first and second planar surfaces can become re-engaged through frictional engagement so that rotation of the first planar surface can cause rotation of the second planar surface.

In certain embodiments, the first planar surface can include a projection that is matingly engageable with a projection receiving notch in the second planar surface. The projection and the notch can be releasably engageable with each other. When the projection and the notch are engaged, rotation of the first planar surface can cause rotation of the second planar surface. When a predetermined torque limit is surpassed, the projection and the notch can become disengaged such that the first planar surface can rotate independently of the second planar surface. Upon further rotation of the first planar surface, the projection can be re-engaged with the notch such that rotation of the first planar surface can cause rotation of the second planar surface.

In some embodiments, the first torque limiting element can include a ball plunger attached to the handle and comprising a ball biased toward the second torque limiting element. The second torque limiting element can include a ball engaging receptacle attached to the rod for releasably engaging the ball plunger ball. In certain embodiments, the ball plunger can be positioned substantially perpendicular to the rod. When the ball plunger ball and the ball engaging receptacle are engaged, rotation of the handle can cause rotation of the rod and surgical implement. When a predetermined torque limit is surpassed upon rotation of the handle, the ball plunger ball and the ball engaging receptacle can become disengaged such that the handle can rotate independently of the rod and surgical implement. Upon further rotation of the handle, the ball plunger ball can be re-engaged with the ball engaging receptacle such that rotation of the handle can cause rotation of the rod and surgical implement.

An embodiment of the present invention can include a kit. Such a kit can include a surgical tool that includes a torque limiting device according to the present invention. The kit may further comprise additional surgical instruments.

Some embodiments of the present invention can include a method of using a surgical tool having a torque limiting device comprising a rod rotatingly engageable on one end with a handle and attached on the opposite end to a surgical implement. A first torque limiting element can be connected to the handle and engageable with a second torque limiting element operably connected to the surgical implement. The surgical implement and a portion of the rod can be inserted into an interior body region, and a first rotational force applied to the handle to rotate the surgical implement. When a second rotational force that exceeds a predetermined torque limit is applied to the handle, the first element can become disengaged from the second element such that the handle rotates without rotation of the surgical implement. Once the two torque limiting elements are disengaged, the handle can be rotated to re-engage the first element with the second element so that further rotation of the handle causes rotation of the surgical implement.

Some embodiments of the present invention can include an axial load limiting system. In an illustrative embodiment, such a system can include a handle having a lever pivotably connected to the handle, a hollow shaft slidably attached to the handle, and a rod operably connected on a proximal end to the lever and movable axially inside the shaft. A surgical implement, for example, a curette, can be connected to the distal end of the rod and pivotably connected to the distal end of the shaft. The system can further include a biasing mechanism, for example, a compression spring, adapted to be compressed within a cavity in the handle by an axial load in excess of a predetermined axial load. When pivoting of the surgical implement is restricted, such as by hard tissue, and the excessive axial load is placed on the rod, the rod and the surgical implement can move the shaft in the distal direction so as to compress the biasing mechanism, thereby relieving the rod and surgical implement of the excessive axial load. In some embodiments, an axial load limiting system can be used in combination with a torque limiting system.

Some embodiments of the present invention can include a method of using a surgical tool having an axial load limiting system. After the surgical tool has been inserted into an interior body region, such as a vertebral body, the lever can be pivoted relative to the handle to pivot the surgical implement. When further pivoting of the surgical implement is restricted due to an obstruction, such as hard tissue, an excessive axial load can be applied to the rod. The excessive axial load can cause the rod, surgical implement, and shaft to be moved in a distal direction so as to compress the biasing mechanism. In this manner, the excessive axial load can be absorbed by the biasing mechanism, thereby relieving the rod, surgical implement, and other attached structures of the surgical tool of the excessive axial load. In an embodiment of such a method in which the surgical implement comprises a curette tip, the handle may be rotated so as to rotate the curette tip and scrape tissue at a surgical site.

Some embodiments of the present invention can include a surgical device, kit, and/or method for interchanging components of the surgical device. In an illustrative embodiment, a surgical device can include a handle, a docking assembly, a shaft assembly, a coupler assembly, and a surgical implement. The handle can have a lever pivotably connected to the handle. The docking assembly can be secured to the handle. The docking assembly can include a docking rod operably attached to the lever and axially slidable within the docking assembly. The shaft assembly can include a shaft rod axially slidable within a detachable shaft and removably attachable to the docking rod. The coupler assembly can be adapted to releasably secure the shaft assembly to the docking assembly. The surgical implement can be attached to a distal end of the shaft rod operable with the lever.

Features of a device, system, kit, and/or method of the present invention may be accomplished singularly, or in combination, in one or more of the embodiments of the present invention. As will be realized by those of skill in the art, many different embodiments of a device, system, kit, and/or method according to the present invention are possible. Additional uses, advantages, and features of the invention are set forth in the illustrative embodiments discussed in the detailed description herein and will become more apparent to those skilled in the art upon examination of the following.

BRIEF DESCRIPTION OF THE DRAWINGS

FIG. 10 is a view of the shaft assembly shown in the embodiment in FIGS. 8 and 9.

FIG. 11 is a view of the proximal portion of the shaft assembly shown in FIGS. 8-10.

DETAILED DESCRIPTION

Figure 1:
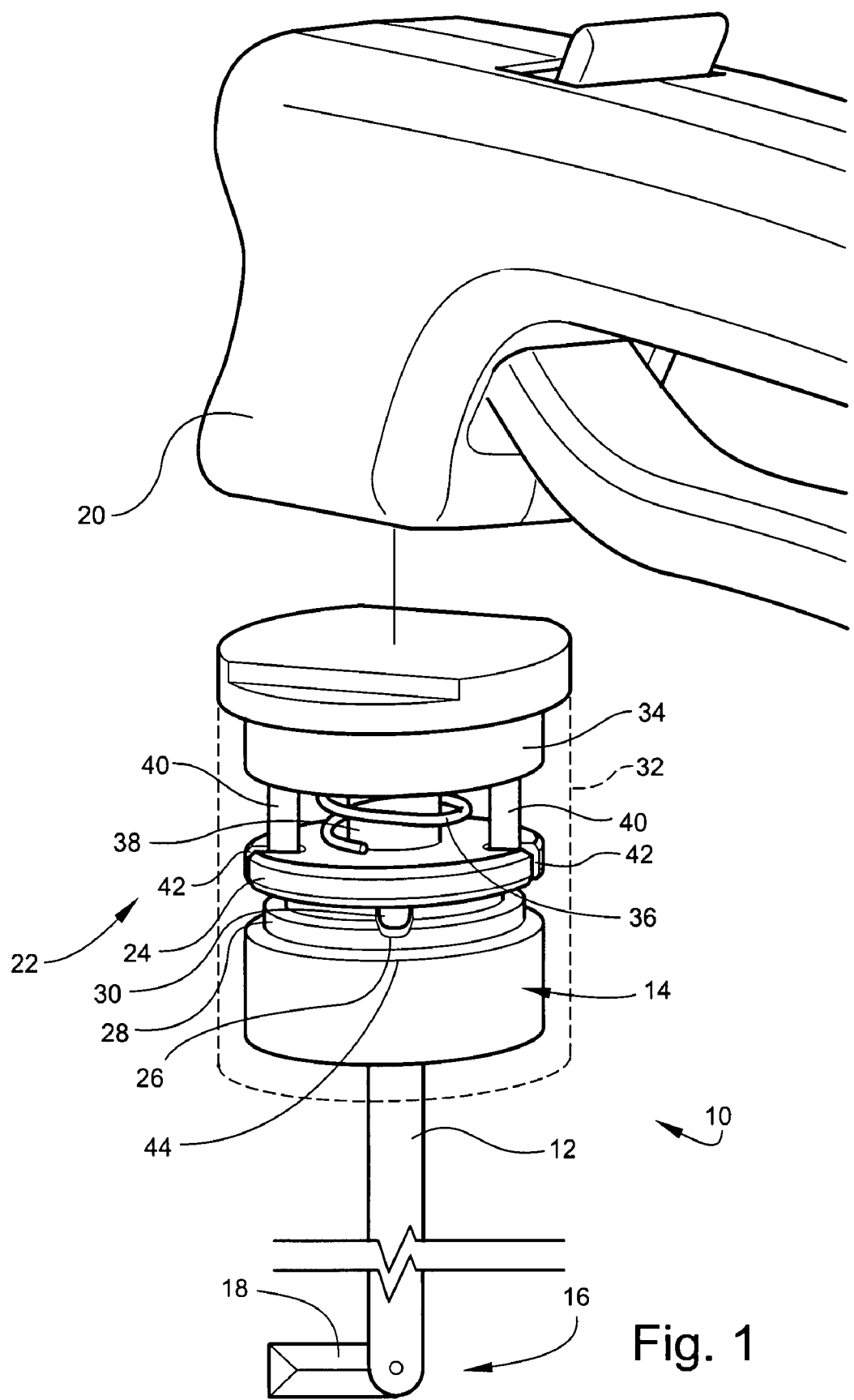
FIG. 1 is a view of a surgical tool having engageable planar surfaces in an embodiment of the present invention.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, for example, 5.5 to 10. Additionally, any reference referred to as being "incorporated herein" is to be understood as being incorporated in its entirety.

As used in this specification and the appended claims, the singular forms "a," "an," and "the" include plural referents unless the context clearly dictates otherwise. Thus, for example, the term "a projection" is intended to mean a single projection or a combination of projections. As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to direction nearer to and farther from, respectively, an operator (for example, surgeon, physician, nurse, technician, etc.) who inserts a medical device into a patient, with the tip-end (i.e., distal end) of the device inserted inside the patient's body. For example, the end of a medical device inserted inside the patient's body is the distal end of the medical device, while the end of the medical device outside the patient's body is the proximal end of the medical device.

In an embodiment, the present invention provides a torque limiting device which may be used with medical devices or other mechanical devices to which a torque is applied. Torque is defined as a turning or twisting force, or the measure of a force's tendency to produce torsion and rotation about an axis. The present invention provides a torque limiting device that may be incorporated into any tool or system that experiences a torque.

In an embodiment, a surgical device of the present invention can comprise a rod attached on one end to a rotatable handle. The rod can be attached on the opposite end to a surgical implement. The surgical device can include a first torque limiting element connected to the handle, and a second torque limiting element operably connected to the rod and surgical implement. The second torque limiting element is releasably engageable with the first torque limiting element. Rotation of the handle when the first and second torque limiting elements are engaged causes rotation of the rod and surgical implement. When a rotational force is applied to the handle that exceeds a predetermined torque limit, the first torque limiting element disengages from the second torque limiting element, so that the handle is rotatable without rotation of the rod and surgical implement. After becoming disengaged, the first torque limiting element is re-engageable with the second torque limiting element so that further rotation of the handle causes rotation of the rod and surgical implement.

In one illustrative embodiment, a torque limiting device according to the present invention may comprise a rod having a first end and second end. The first and second ends may include the respective tip of the rod as well as a region of the rod near that tip. The device may further comprise a handle rotatably attached to the first end of the rod and a surgical implement fixedly attached near the second end of the rod. The device may further comprise a first surface attached to the handle and a second surface attached to the rod. The two surfaces may be disposed in frictional contact with each other, for example via a projection and a notch. The two surfaces may be contained within a housing, which may be attached to the handle.

The device may further comprise a biasing mechanism, such as a spring, positioned between the housing and the first surface to force the projection into the notch when the projection and notch are aligned. The two surfaces are able to rotate independently, but when the projection and notch are engaged, the two surfaces rotate together. The projection and notch may be designed to disengage when a torque equal to or greater than a predetermined torque limit is applied to the device. The torque limit can be the torque that is required to cause the projection to overcome the static friction force between the surfaces and the spring force exerted by the spring on the first surface such that the projection disengages from the notch. When the projection disengages from the notch, the two surfaces rotate independently, and consequently the excessive torque applied to the first surface is not translated to the second surface. The two surfaces may be made of a polymer, stainless steel, aluminum, or any other material or combination of materials suitable for creating friction between the two surfaces.

This torque limiting device may be used, for example, on a curette. A curette may comprise the elements disclosed in PCT Patent Application WO 2005/023085, which is incorporated herein by reference in its entirety. The disengagement of the projection from the notch protects the curette tip, for example, from an application of torque that may be sufficient to break the tip while still inserted in a patient.

In addition to limiting the amount of torque that can be applied to the functional implement of the tool, the device of the present invention may be re-engaged to resume use. After the projection disengages from the notch, the device may be re-engaged by rotating the first surface until the projection and notch re-align, at which point the spring forces the projection into the notch. When the projection and notch are engaged again, the use of the tool may resume. The ability to re-engage the device is a advantageous over conventional devices, which may suffer permanent damage when an excessive torque is applied. Therefore, conventional torque limiting devices are unable to be used after one instance of excessive torque, whereas a torque limiting device of the present invention may be reused after many instances of excessive torque.

The torque limiting device of the present invention may be used in medical tools, such as a curette, as described above. The torque limiting device may be used in other surgical tools for use in human and veterinary applications, including tools for grasping, scraping, bending, pushing, or otherwise manipulating tissue or an organ, including bone. The device may be used in other tools or machines in which a maximum torque should not be exceeded. For example, the torque limiting device of the present invention can be included in a screwdriver or wrench to prevent over-tightening of a screw or bolt. The torque limiting device may also be used on machines in which certain components could break when excessive torque is applied.

Figure 2:
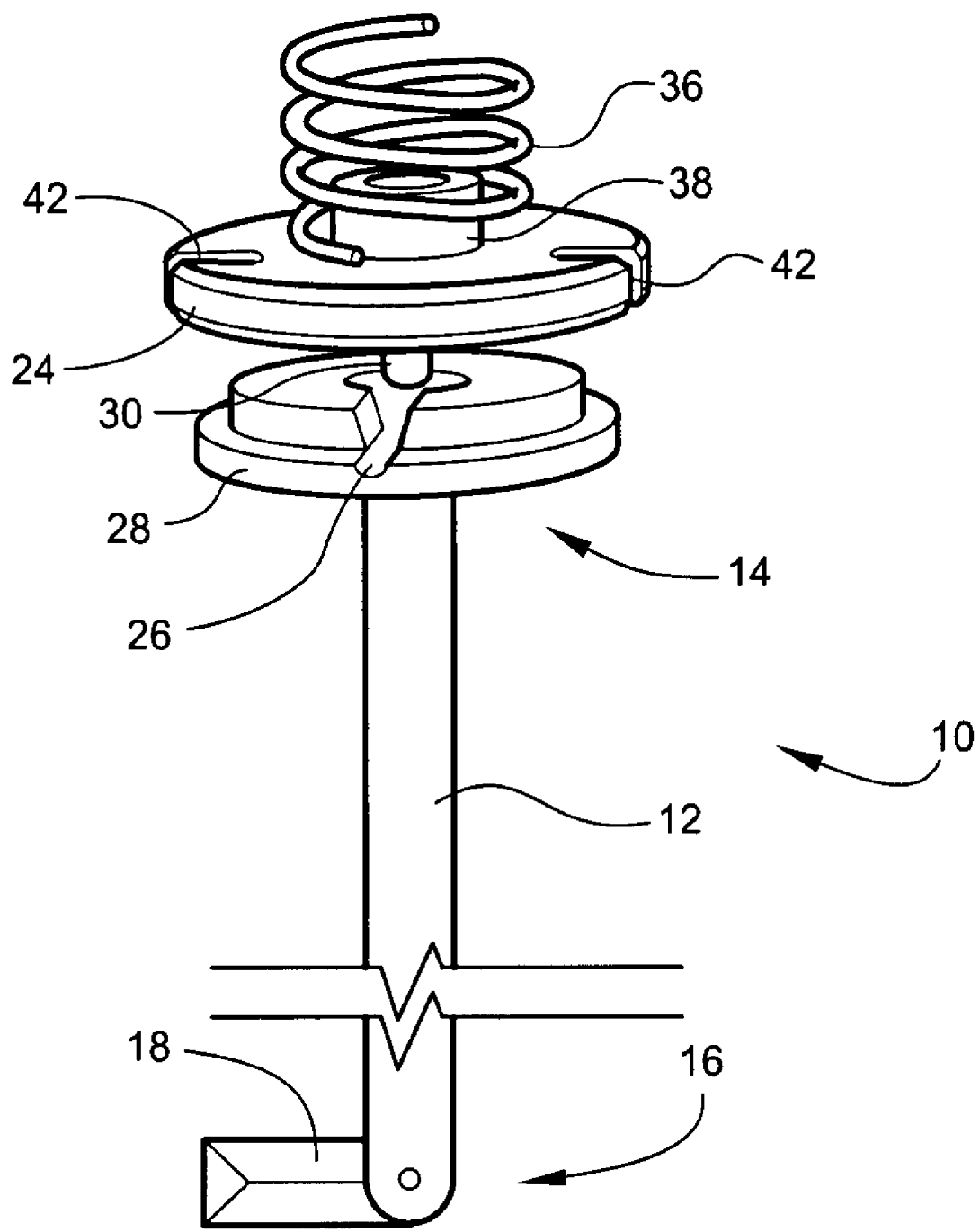
FIG. 2 is a view of a portion of the embodiment of the surgical tool shown in FIG. 1, showing disengagement of the planar surfaces.
Figure 3:
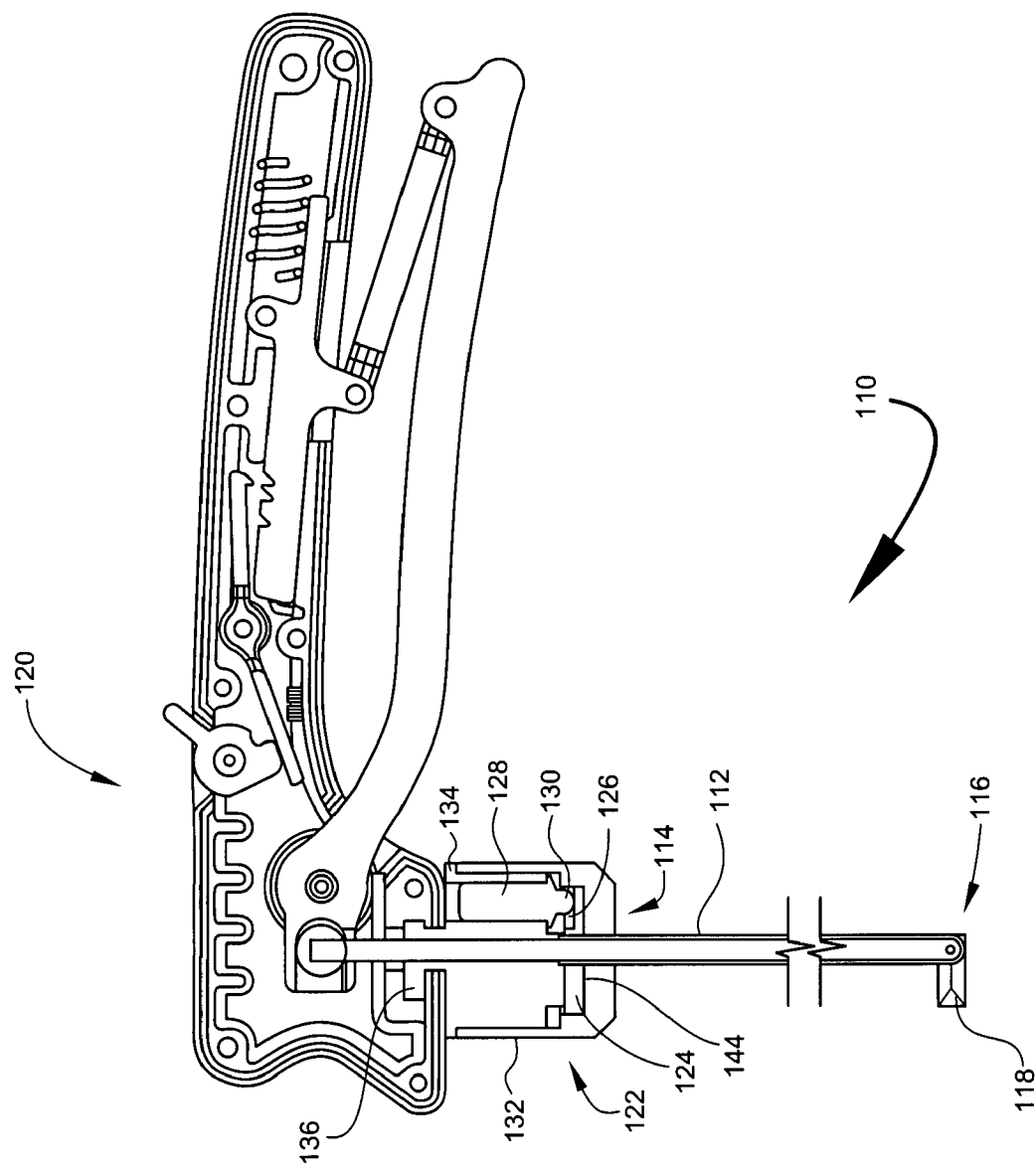
FIG. 3 is a cross-sectional view of a surgical tool in an embodiment of the present invention.
Figure 4:
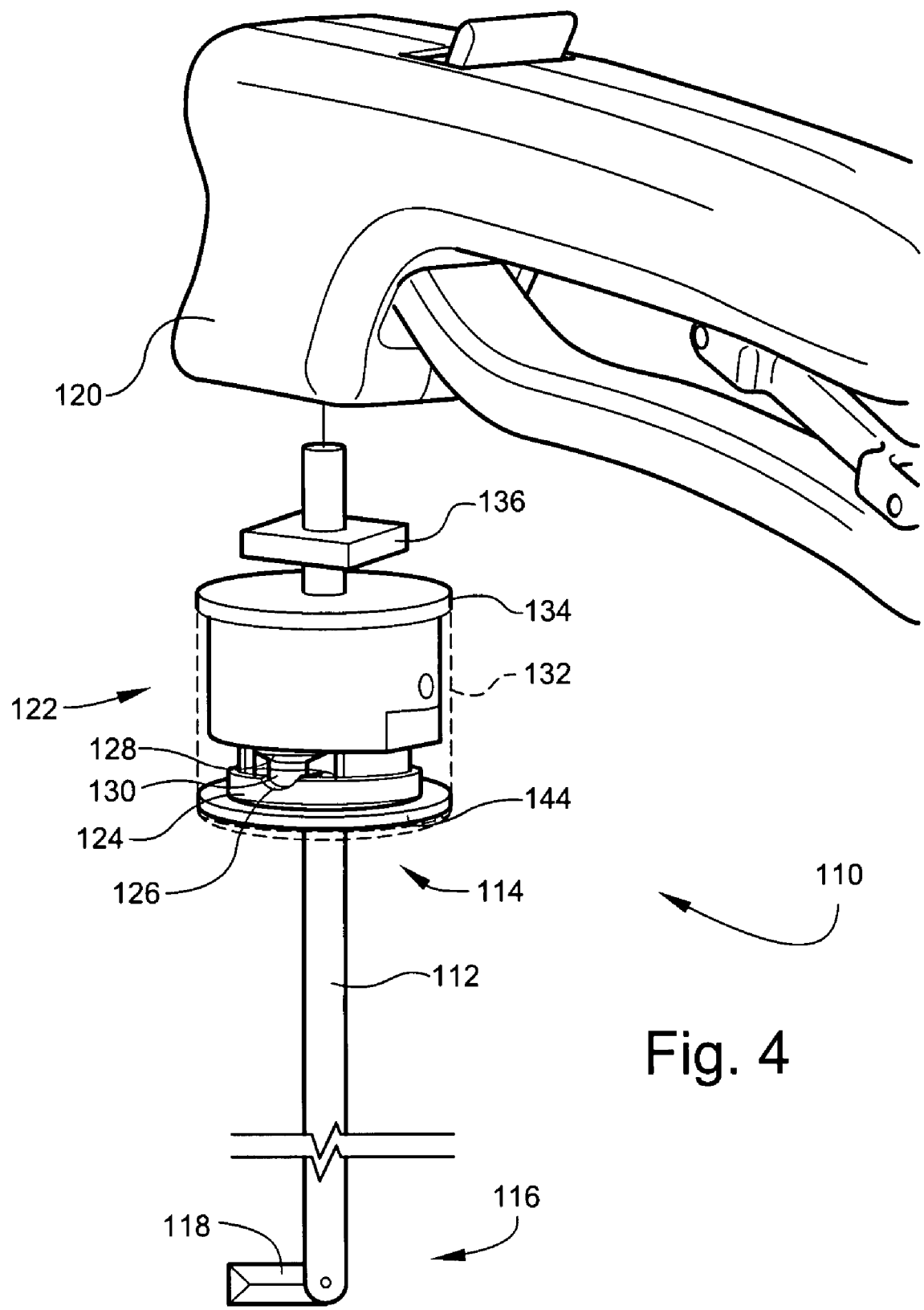
FIG. 4 is a view of the embodiment of the surgical tool shown in FIG. 3, showing engagement of the planar surfaces.
Figure 5:
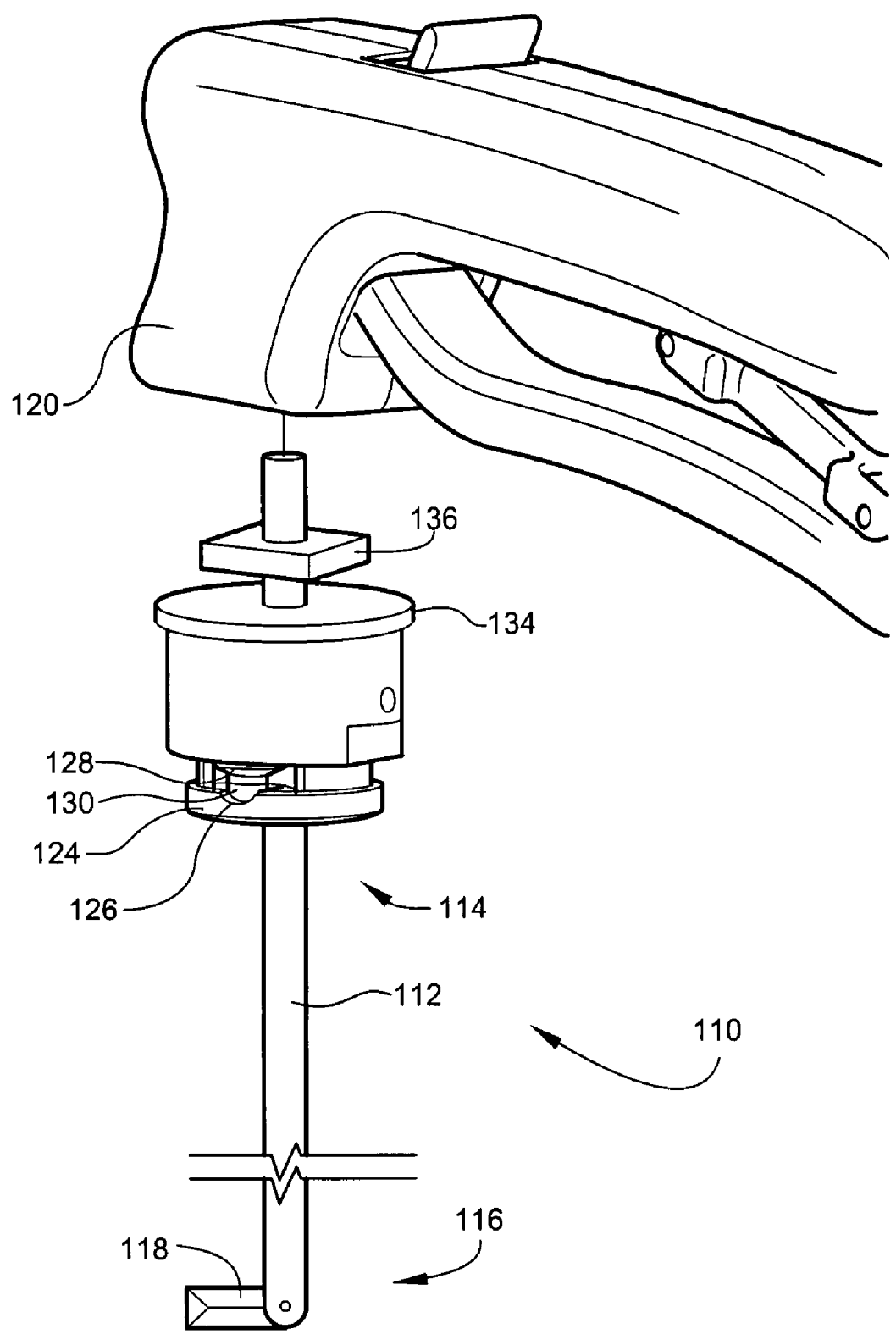
FIG. 5 is a view of a portion the embodiment of the surgical tool shown in FIGS. 3 and 4.
Figure 6:
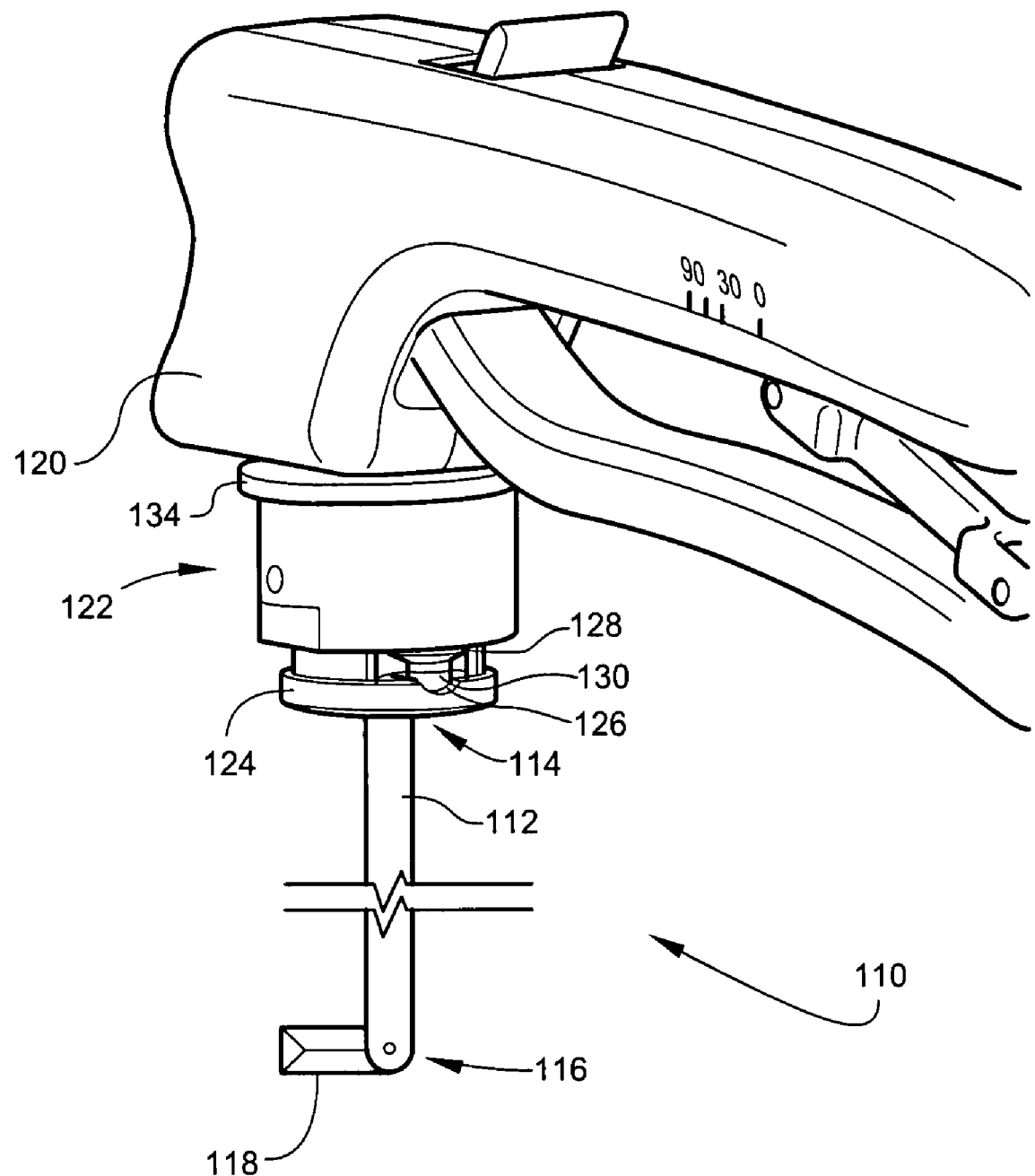
FIG. 6 is a perspective view of the embodiment of the surgical tool shown in FIGS. 3, 4, and 5.

Referring now to FIGS. 1-2, in one embodiment of the present invention, a surgical tool 10 may comprise a rod 12 having a first end 14 and a second end 16. The first end 14 and second end 16 may each comprise a tip of the rod 12 as well as a region of the rod 12 proximate each tip. A handle 20 may be positioned near the first end 14 of the rod 12, and the handle 20 may be manipulated by a user. A surgical implement 18 may be coupled or fixedly attached to the second end 16 of the rod 12. A torque limiting device 22 may be attached to the handle 20 and to the rod 12, so that rotation of the handle 20 causes rotation of the rod 12, and therefore, of the surgical implement 18.

The torque limiting device 22 may comprise a first plate 24 having a projection 30 and a second plate 28 having a notch 26. The notch 26 and projection 30 can be interchangeable, that is, the first plate 24 can have the notch 26 and the second plate 28 can have the projection 30. The projection 30 and notch 26 may be substantially the same shape and size so that they can fit together. The projection 30 may be V-shaped, V-shaped with a flat bottom, U-shaped, semi-circular, or any other shape that provides a non-perpendicular angle between the projection 30 and the surface of the second plate 28. The projection 30 and the notch 26 may be radially aligned such that the projection 30 fits into the notch 26 when they are rotationally aligned.

The first plate 24 and the second plate 28 may be disposed within a housing 32. The housing 32 may be generally in the shape of a hollow cylinder having an inner diameter equal to or larger than the diameter of the larger of the first plate 24 and the second plate 28. The housing 32 may comprise a cap 34, and a biasing mechanism, such as compression spring 36, may be disposed between the cap 34 and the first plate 24. The first plate 24 may include a collar 38 over which the spring 36 fits so that lateral movement of the spring 36 is substantially prevented. The torque limiting device 22 may further comprise at least one guide pin 40, and the first plate 24 may comprise at least one slot 42. The at least one guide pin 40 may be integrally formed with the cap 34 or with the housing 32, or the at least one guide pin 40 may be fixedly attached to the cap 34 or to the housing 32. The first plate 24 may be positioned in the housing 32 such that the at least one guide pin 40 fits into the at least one slot 42. The at least one slot 42 allows the first plate 24 to slide longitudinally along the at least one guide pin 40 and prevent the first plate 24 from rotating with respect to the housing 32. The first plate 24 will then rotate only when the housing 32 rotates.

Conversely, the second plate 28 may be disposed in the housing 32 such that rotational movement of the second plate 28 with respect to the housing 32 is allowed but longitudinal movement with respect to the housing 32 is prevented. This may be accomplished by providing the housing 32 with a support 44, such as a ledge, that contacts the bottom surface of the second plate 28, or by other suitable means. Accordingly, the second plate 28 is permitted to rotate about the support 44 but is not permitted to move longitudinally along the rod 12.

The rod 12 may be integrally formed with the second plate 28 or may be fixedly attached to the second plate 28, such as by welding. Therefore, rotation of the second plate 28 is directly translated to the rod 12, and consequently to the surgical implement 18.

In an embodiment, the housing 32 may be attached to the handle 20. As such, rotation of the handle 20 can be directly translated to the housing 32, and consequently, via the at least one guide pin 40, to the first plate 24.

Rotation of the first plate 24 is translated to the second plate 28 by the frictional interface between the projection 30 and the notch 26. When the projection 30 and notch 26 are engaged, that is, when the projection 30 and notch 26 are rotationally aligned and the projection 30 is positioned within the notch 26, rotation of the handle 20 causes rotation of the surgical implement 18. The frictional engagement interface between the first plate 24 and the second plate 28 that provides for translation of the torque applied to the first plate 24 to rotate the second plate 28 can be referred to as a torque translation interface.

However, if a torque above a predetermined torque limit is applied to the handle 20, the engaging friction force between the projection 30 and notch 26 and the spring force of the compression spring 36 against the first plate 24 may be overcome. When these forces are overcome, and the projection 30 may disengage from the notch 26, such that the projection 30 releases from the notch 26 and the projection 30 and the notch 26 are no longer rotationally aligned. When the projection 30 is disengaged from the notch 26, a rotation of the handle 20 does not cause a rotation of the implement 18. The projection 30 and notch 26 may be engaged again by rotating the handle 20 until the projection 30 and notch 26 are rotationally aligned, at which point the compression spring 36 will push the projection 30 into the notch 26 again.

The predetermined torque limit may be determined by varying any one or more of the following or combination of the following: the spring rate of the compression spring 36; the relative slopes of the projection 30 and notch 26; the length and depth of the notch 26; the height of the projection 30; the radial distance of the projection 30 and notch 26 from the center of the first and second plates 24, 28, respectively; and the materials used for the plates 24, 28. Spring rate is a measure of the compressive force potential of a compression spring. Spring rate is expressed as the spring constant "k" for a compression spring that exerts a force "F" when an applied load deforms the spring from a free length to particular deformed length. The spring rate constant is calculated as $k = F/L_{free} - L_{def}$.

In an embodiment, the surgical tool 10 of the present invention may be designed to begin to disengage the torque translation interface at, for example, about 10±1 in.-lbs. torque and to completely disengage at, for example, about 13±1 in.-lbs. torque. Thus, if a torque of 13 in.-lb., for example, is required to completely disengage the torque translation interface (such as the coupling of the first and second plates 24, 28, respectively, between the handle 20 and the surgical implement 18), the projection 30 and notch 26 may be designed to begin to disengage when a torque of approximately 10 in.-lb, for example, is applied to the handle 20, and to completely disengage when 13 in.-lb. torque is applied to handle 20. As a result, a torque greater than the predetermined torque limit, for example, a torque of 15 in.-lb., cannot be translated to the rod 12 because the projection 30 will disengage from the notch 26 at a torque of 13 in.-lb. It has been found that the mean torque required to scrape normal bone with a curette is approximately 2.0 in.-lb. Therefore, a torque limiting device adapted 22 that causes disengagement to begin at 10 in.-lb and to complete at 13 in.-lb. can allow a torque that is required for normal bone scraping to be translated to the surgical implement.

Referring now to FIGS. 3-6, in another embodiment of the present invention, a surgical tool 110 may comprise a rod 112 having a first end 114 and a second end 116. The first end 114 and second end 116 may each comprise a tip of the rod 112 as well as a region of the rod 112 proximate each tip. A handle 120 may be positioned near the first end 114 of the rod 112, and the handle 120 may be manipulated by a user. A surgical implement 118 may be coupled or fixedly attached to the second end 116 of the rod 112. A torque limiting device 122 may be attached to the handle 120 and to the rod 112, so that a rotation of the handle 120 causes a rotation of the rod 112, and therefore, of the surgical implement 118.

The torque limiting device 122 may comprise a plate 124 having a depression 126 and a ball plunger 128 having a ball 130. The ball 130 and depression 126 may be substantially the same shape and size so that they can fit together. The ball 30 may be V-shaped, V-shaped with a flat bottom, U-shaped, semi-circular, or any other suitable shape. The ball 130 and the depression 126 may be radially aligned such that the ball 130 fits into the depression 126 when they are rotationally aligned. The ball plunger 128 may comprise other components (not shown), as will be apparent to those of skill in the art of surgical instrument design. For example, the ball plunger 128 may comprise a hollow cylinder, partially within which the ball slides longitudinally. The ball plunger 128 may also comprise a shaft that limits the movement of the ball 130 and a biasing mechanism, such as a spring, that tends to push the ball 130 longitudinally in the cylinder. The ball plunger 128 may also have other configurations that allow for longitudinal movement of the ball 130.

The plate 124 and the ball plunger 128 may be disposed within a housing 132. The housing 132 may be generally in the shape of a hollow cylinder having an inner diameter equal to or larger than the diameter of the plate 124. The housing 132 may comprise a cap 134, and the ball plunger 128 may be mounted or attached to the cap 134. In such an embodiment, rotation of the housing 132 results in a rotation of the ball plunger 128.

The plate 124 may be disposed within the housing 132 such that rotational movement of the plate 124 is allowed but longitudinal movement with respect to the housing 132 is prevented. This may be accomplished by providing the housing 132 with a support 144, such as a ledge, that contacts the bottom surface of the plate 124, or by other suitable means.

The rod 112 may be integrally formed with the plate 124 or may be fixedly attached to the plate 124, such as by welding. As such, rotation of the plate 124 can be directly translated to the rod 112, and consequently to the surgical implement 118.

The housing 132 may further comprise a flange 136 attached to the cap 134. The handle 120 may be attached to the housing 132 by fitting over the flange 136 in a relatively tight tolerance. Accordingly, rotational movement of the handle 120 can be translated through the flange 136 to the housing 132, and in turn to the ball plunger 128.

Rotation of the ball plunger 128 is translated to the plate 124 by the frictional engagement interface between the ball 130 and the depression 126. When the ball 130 and depression 126 are engaged, that is, when the ball 130 and depression 126 are rotationally aligned and the ball 130 is positioned within the depression 126, rotation of the handle 120 causes rotation of the surgical implement 118. The frictional engagement interface between the ball 130 and the depression 126 that provides for translation of the torque applied to the plate 124 to rotate the surgical implement 118 can be referred to as a torque translation interface.

However, when the torque applied to the handle 120 exceeds a certain predetermined torque limit, the ball plunger 128 may be compressed and the ball 130 of the ball plunger 128 rises out of engagement with the depression 126 to a disengaged position. When the ball 130 and depression 126 are disengaged, rotation of the handle 120 no longer causes a rotation of the surgical implement 118. The ball 130 and depression 126 may be engaged again by rotating the handle 120 until the ball 130 and depression 126 are rotationally aligned, at which point the ball plunger 128 can extend so that the ball 130 again rests in engagement within the depression 126.

The maximum torque limit may be determined by varying any one or more of the following or combination of the following: the spring rate of the compression spring in the ball plunger 128; the shape and size of the ball 130 and depression 126; the radial distance of the ball 130 and depression 126 from the center of the plate 124; and the materials used for the ball 130 and the plate 124.

FIGS. 8-11 illustrate another embodiment of the present invention. In such an embodiment, a surgical tool 10 may comprise a shaft assembly 150 having a proximal end 151 and a distal end 152. The proximal end 151 and the distal end 152 of the shaft assembly 150 may each comprise a tip of the shaft assembly 150 as well as a region of the shaft assembly 150 proximate each tip. The shaft assembly 150 can include a hollow shaft 153 having a ball engaging receptacle, for example, the ball detent collar 154, fixed to the outer surface of the proximal end 151 of the shaft 153. A rod 155 having a length greater than the length of the shaft 153 can be inserted into the shaft 153. The rod 155 can include a ball joint 156, as shown best in FIGS. 10 and 11, attached at the proximal end 151 of the rod 155.

Figure 8:
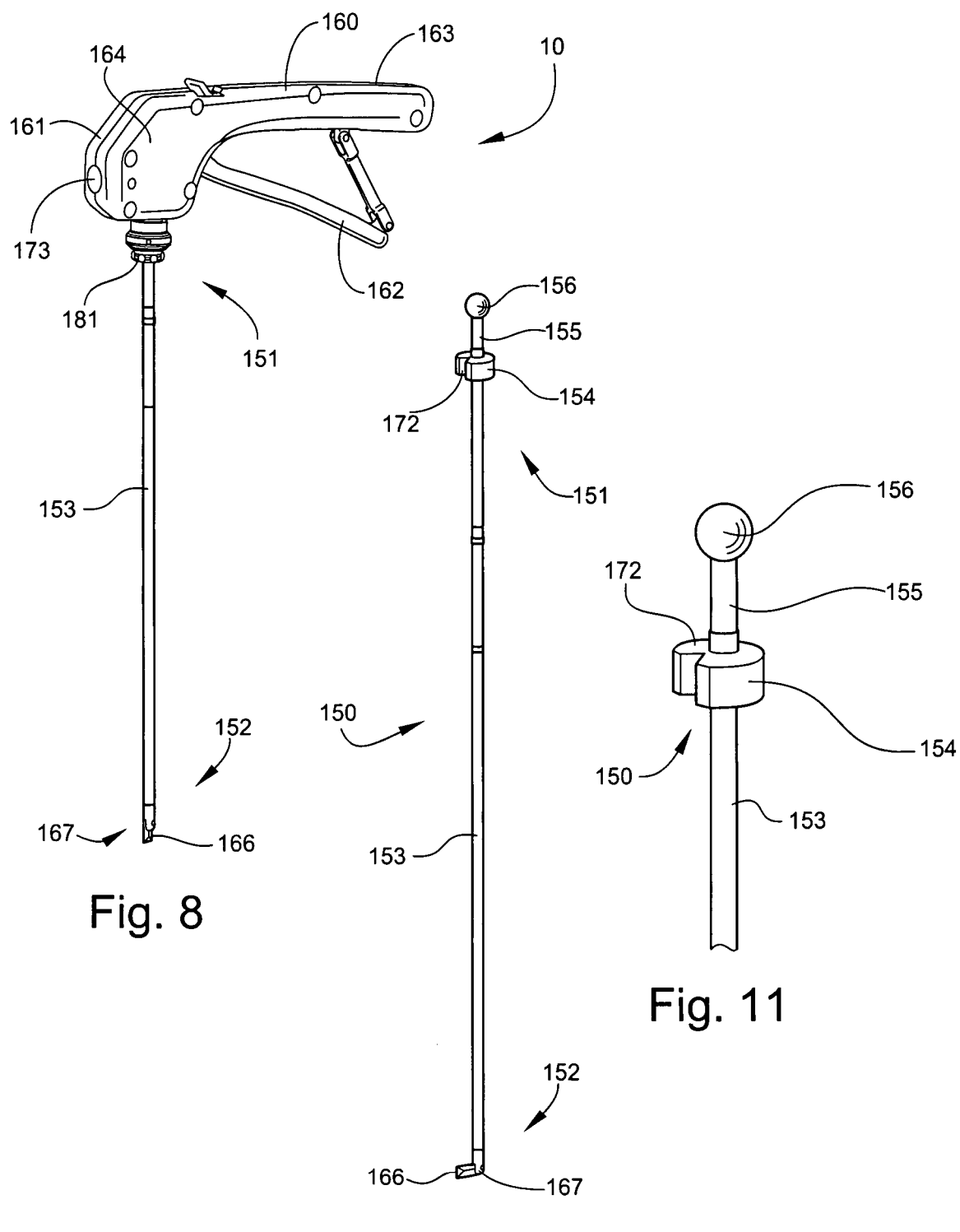
FIG. 8 is a view of a surgical tool in another embodiment of the present invention.
Figure 9:
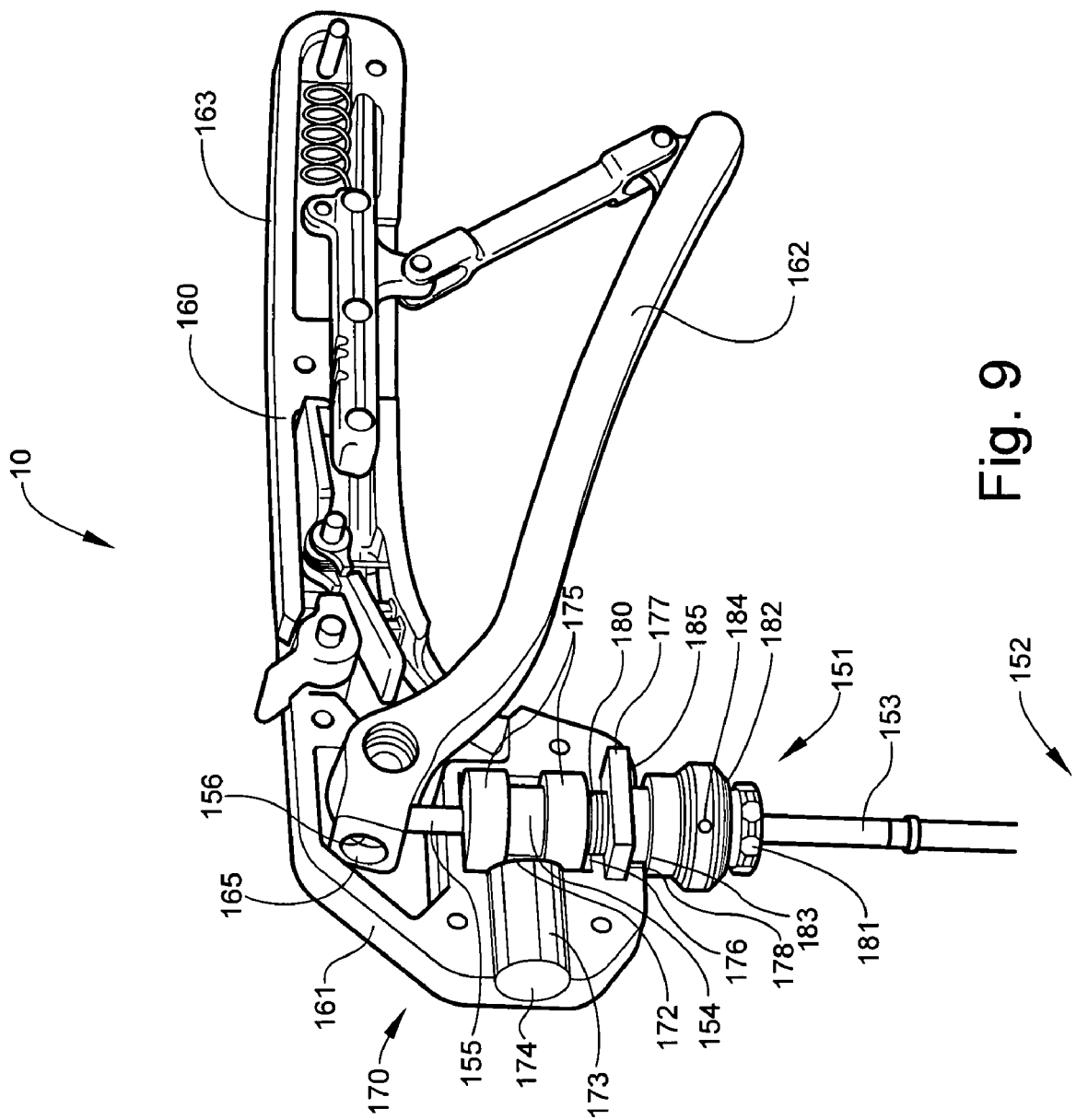
FIG. 9 is a close-up view of the handle of the embodiment of the surgical tool shown in FIG. 8, with part of the handle housing removed to show the internal components of the handle.

A handle 160 may be operably connected to the proximal ends 151 of the rod 155 and the shaft assembly 150, and the handle 160 may be manipulated by a user. FIG. 8 shows the handle 160 as assembled with the shaft assembly 150. FIG. 9 shows the handle 160 with one side of the handle housing 161 removed to illustrate the internal configuration and operation of the handle 160 and associated components of the surgical tool 10. The surgical tool 10 can include a lever 162 hingedly attached on one end to the grip portion 163 of the handle 160 and pivotably attached on the opposite end to the head 164 of the handle 160 within the handle housing 161. As shown in FIG. 9, the lever 162 can be configured on the end attached to the head 164 of the handle 160 to include a ball joint receptacle 165, or socket, for receiving the ball joint 156 at the proximal end 151 of the rod 155 and thereby operably connect the lever 162 to the rod 155.

A surgical implement 166 may be attached to the distal end 152 of the rod 155, as shown in FIGS. 8 and 10. As shown in this embodiment, the surgical implement 166 can be a curette. However, the surgical implement 166 can be any surgical implement adaptable for use at the end of a rod 155 as described. As shown in FIG. 8, the curette can be aligned with the longitudinal axis of the rod 155 and shaft 153, which may be a preferred position for the curette as the surgical tool 10 is being inserted into a patient's interior body region. When the tool 10 is in a desired position in the patient's body, the curette can be articulated about a joint 167 in the rod 155 that extends beyond the distal 152 tip of the shaft 153 such that the curette can be moved into a different position. For example, the curette may be moved to a desired position with a range of positions from alignment with the longitudinal axis of the rod 155 to a position about 135 degrees from the aligned position (that is, forming an angle of about 45 degrees with the rod). One preferred position for use of the curette is substantially perpendicular with the longitudinal axis of the rod 155. Such articulation of the curette about the joint 167 can be achieved by movement of the lever 162 toward or away from the grip portion 163 of the handle 160. As the lever 162 is moved toward the grip portion 163 of the handle 160, the pivotable end of the lever 162 pivots in the distal direction, causing the ball joint 156 and the attached rod 155 to move in the distal direction. As the rod 155 moves in the distal direction, the curette articulates about the joint 167 and moves out of alignment with the rod 155 and into an angled position relative to the rod 155. As the lever 162 is moved away from the grip portion 163 of the handle 160, the pivotable end of the lever 162 pivots in the proximal direction, causing the ball joint 156 and the attached rod 155 to move in the proximal direction. As the rod 155 moves in the proximal direction, the curette articulates about the joint 167 and moves toward alignment with the rod 155. In this manner, the curette can be moved into various desired positions for scraping tissue in an interior body region.

In the embodiment shown in FIGS. 8-11, a torque limiting device 170 may be attached to the handle 160 and to the shaft assembly 150, so that rotation of the handle 160 causes rotation of the shaft assembly 150 and rod 155, and, in turn, rotation of the surgical implement 166. The torque limiting device 170 can include a first torque limiting element releasably engageable with a second torque limiting element. The torque limiting device 170 can comprise a ball plunger (not shown) having a ball, or engaging end, and the ball engaging receptacle, or ball detent collar, 154 having a detent 172, in its outer surface. The ball plunger and engaging ball may be similar to the ball plunger 128 and ball 130 shown in FIG. 3. The ball detent collar 154 can be fixed to the proximal end 151 of the shaft 153. The detent 172 in the ball detent collar 154 can be a notch, depression, or other void configured to receive and engage the ball of the ball plunger. The engaging ball may be rounded, semi-circular, U-shaped, V-shaped, V-shaped with a flat bottom, or any other suitable shape that allows for engagement and disengagement with the ball detent 172.

The ball plunger and attached engaging ball can be housed in a ball plunger housing 173. As shown in the embodiment in FIGS. 8-11, the ball plunger housing 173 can be seated in a depression in the handle housing 161 and can be aligned perpendicularly with the ball detent collar 154 such that the engaging ball is engageable with the detent 172 in the ball detent collar 154. The ball plunger housing 173 may comprise a hollow cylinder, within which the ball plunger and engaging ball can slide at least partially along the longitudinal axis of the ball plunger housing 173. A biasing mechanism (not shown), for example, a compression spring, can be positioned between the outer end 174 of the ball plunger housing 173 and the ball plunger so as to bias the ball plunger longitudinally in the ball plunger housing 173 toward the ball detent 172 in the ball detent collar 154. The ball plunger housing 173, biasing mechanism, ball plunger, and engaging ball may include other components (not shown) and/or have other configurations that allow for longitudinal movement of the ball plunger into and out of engagement with the ball detent 172.

The engaging ball and the detent 172 in the ball detent collar 154 may be matingly configured such that the ball can engage the detent 172 so that the ball detent collar 154 and attached shaft 153 can be rotated when the handle 160 is rotated. A frictional engagement interface between the engaging ball and the ball detent 172 can allow rotational force applied to handle 160 and the ball plunger to be translated to the shaft 153. When the ball and ball detent 172 are engaged, that is, when the ball and ball detent 172 are rotationally aligned and the ball is positioned within the detent 172, rotation of the handle 160 causes rotation of the surgical implement 166. The frictional engagement interface between the engaging ball and the ball detent 172 that provides for translation of the torque applied to the handle 160 to rotate the surgical implement 166 can be referred to as a torque translation interface.

When a user applies pressure to rotate the handle 160 beyond a predetermined torque limit, the ball plunger may be compressed and the engaging ball rises out of engagement with the ball detent 172 to a disengaged position. That is, the engaging ball and the ball detent 172 can be releasably engageable. When the ball and ball detent 172 are disengaged, rotation of the handle 160 no longer causes a rotation of the surgical implement 166. When the handle 160 is rotated while the engaging ball is disengaged from the ball detent 172, the handle 160 rotates about the rod 153 by means of the ball joint receptacle 165 in the lever 162 rotating about the ball joint 156 of the rod 153. In this way, the handle 160 can be disengaged from the shaft assembly 150, and breaking of the surgical tool 10 from too great a torque can be avoided. The configurations of the engaging ball and the ball detent 172 can also provide for disengagement of the ball from the detent 172 when a predetermined torque limit caused by rotation of the handle 160 is surpassed. When the engaging ball becomes disengaged from the ball detent 172 on the shaft 153, the handle 160 can be freely rotated to reposition the ball plunger, and engaging ball, back into the ball detent 172 to re-engage the handle 160 with the shaft assembly 150. In addition to avoiding breaking of the surgical tool 10, use of the tool can be readily resumed without removing the tool 10 to repair or reset it for further use. These features may avoid injury to a patient and decrease surgical time related to broken surgical tools.

As shown in FIG. 8, the ball detent collar 154 may be in rotatable contact with a thrust bearing 175 adjacent the proximal surface, or top, of the collar 154 and with another thrust bearing 175 adjacent the distal surface, or bottom, of the collar 154. In this embodiment, each of the thrust bearings 175 is embedded, or fixed, in a mating cavity 176 in the handle housing 161. Ball bearings (not shown) are located at the interface between the thrust bearings 175 and the ball detent collar 154. The thrust bearings 175 can help reduce friction between the ball detent collar 154 and the handle 160 when the ball plunger is disengaged from the ball detent 172 and the handle 160 is rotated freely about the shaft assembly 150 after a predetermined torque limit is surpassed.

The surgical tool 10 may include a mechanism for further securing the shaft assembly 150 to the handle 160. As shown in FIG. 9, one such mechanism includes a hub 177, or plate, having a threaded bore fixed to the handle housing 161. For example, the hub 177 can include a notch 178 that is configured to securely fit about a mated portion of the handle housing 161 so as to fix the hub 177 to the handle housing 161. A "through hole" bolt 180 can then be threaded through the threaded bore of the hub 177. In an alternative embodiment, the hub 177 is not used and the handle housing 161 below the distal, or lower, thrust bearing 175 can be threaded to receive the through hole bolt 180. The through hole bolt 180 has a hole through the center of the length of the bolt 180. The through hole bolt 180 can be slid over the distal end 152 of the shaft 153 through the center hole in the bolt 180 and threaded through the threaded bore of the hub 177. A thumb wheel 181 on one end of the through hole bolt 180 can be rotated to thread the bolt 180 through the hub 177. The through hole bolt 180 can include a set screw support collar 182 positioned about the outer circumference of the bolt 180. The bolt 180 can be threaded through the hub 177 such that the upper edge 183 of the set screw support collar 182 abuts the distal, or bottom, edge 185 of the handle housing 161. When the set screw support collar 182 is in position abutting the handle housing 161, a set screw 184 can be inserted through the set screw support collar 182 and into contact with the outer surface of the through hole bolt 180. In this manner, any clearance, or "slack," between the thrust bearings 175 and the shaft assembly 150, including the ball detent collar 154, is reduced or eliminated. As such, any radial or axial movement of the shaft assembly 150 relative to the handle 160 when the handle 160 is engaged with the shaft assembly 150 can be prevented.

Rotation of the ball plunger in the handle 160 can be translated to the shaft 153 by the frictional interface between the engaging ball and the ball detent 172. When the ball and ball detent 172 are engaged, that is, when the ball and ball detent 172 are rotationally aligned and the ball is positioned within the detent 172, rotation of the handle 160 causes rotation of the surgical implement 166. However, when the torque applied to the handle 160 exceeds a certain predetermined torque limit, the ball plunger may be compressed and the engaging ball rises out of engagement with the ball detent 172 to a disengaged position. When the ball is disengaged from the ball detent 172, rotation of the handle 160 no longer causes rotation of the surgical implement 166. The ball and ball detent 172 may be engaged again by rotating the handle 160 until the ball and ball detent 172 are rotationally aligned, at which point the ball plunger can extend so that the engaging ball again rests in engagement within the ball detent 172.

The maximum torque limit in the embodiment of the torque limiting device 170 shown in FIGS. 8-11 may be determined by varying any one or more of the following or combination of the following: the spring rate of the compression spring in the ball plunger; the shape and size of the engaging ball (not shown) of the ball plunger; the size and shape of the ball detent 172; the radial distance of the ball detent 172 from the shaft 153; and the materials used for the ball plunger ball and the ball detent 172.

Figure 7:
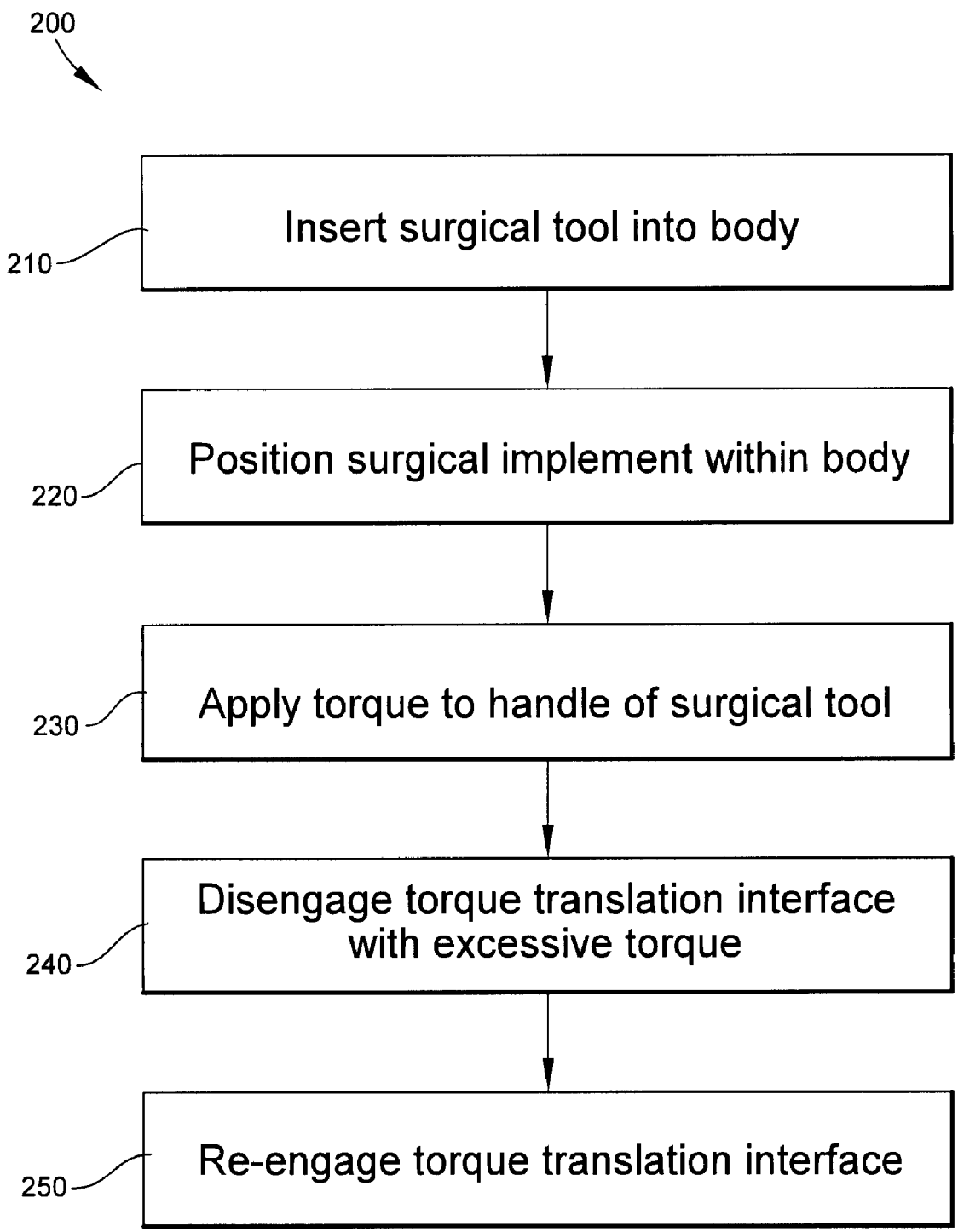
FIG. 7 is a block diagram representation of an embodiment of a method of the present invention.

The present invention may include embodiments of a method for using the torque limiting device 22, 122 as described herein. Referring now to FIG. 7, the illustrated embodiment of the method 200 comprises inserting 210 a surgical tool into a body, the surgical tool having a handle having a torque translation interface with a rod, the rod being attached to a surgical implement. The surgical implement, such as the curette, can be positioned 220 at a desired location within the body. Torque can then be applied 230 to the handle to cause the rod and the surgical implement to rotate. The method further includes disengaging 240 the torque translation interface between the handle and the rod by applying a torque greater than a predetermined torque limit. The method may further include re-engaging 250 the torque translation interface after an excessive torque has caused its disengagement. In an embodiment, the torque translation interface can comprise a first surface of the surgical tool and a second surface of the surgical tool. One of the surfaces can include a projection 30 engageable with a notch 26 in the other surface. Re-engaging 240 the first surface with the second surface may comprise rotating the handle until the projection 30 and the notch 26 are re-aligned for re-engagement.

In another aspect of the present invention, an embodiment of the surgical tool 10 can include an axial load limiting system 186. As shown in FIGS. 12-18, in such an embodiment, a biasing mechanism may be secured in a position axially about the hollow shaft 153 within the cavity 176 in the handle housing 161. The biasing mechanism can be set to remain stationary in the position within the cavity 176 until a predetermined axial load threshold on the biasing mechanism is reached.

In certain embodiments, as shown in FIGS. 12-13 and 16-18, the cavity 176 in the handle housing 161 can have threads 189 for receiving a threaded object, such as a matingly threaded bolt 191. The threaded bolt 191 can be hollow, and the biasing mechanism may be placed inside the hollow threaded bolt 191. The biasing mechanism can be a spring 188, such as a compression spring, a coil spring, an extension spring, or a torsion spring. With the spring 188 inside the bolt 191, the spring 188 and bolt 191 can be slid over the hollow shaft 153 and the bolt 191 threaded into the threads 189 of the handle cavity 176 to a preset point. A spring securing mechanism may then be fastened to the handle 160 and in contact with distal surfaces of the bolt 191 and the spring 188 so as to maintain the spring 188 in an initially stationary position until an axial load in excess of the predetermined axial load on the spring 188 is reached. The spring securing mechanism may be, for example, a lock nut 190. As shown in FIGS. 12-13 and 16-18, the lock nut 190 can then be slid over the hollow shaft 153 and fastened into position about the shaft 153 in contact with the bottom surface of the threaded bolt 191 so as to maintain the bolt 191 in an initially constant position inside the handle housing 161. The lock nut 190 may be fastened into position in a variety of ways, including, for example, threading the nut 190 onto threads made in the exterior surface of the handle housing 161 and/or inserting a set screw through the nut 190 into contact with the handle housing 161. In this manner, the spring 188 can be set to remain in stationary position until a predetermined axial load threshold on the spring 188 is reached.

A spring compression collar 187 can be fixedly attached to or formed integrally with the exterior of the hollow shaft 153 near the proximal end 151 of the shaft 153 so as to fit inside the handle cavity 176. The spring compression collar 187 can be configured to move in a downward and upward axial motion within the handle cavity 176 with respect to the longitudinal axis 157 of the hollow shaft 153. The spring 188 can be configured to extend upward beyond the top of the hollow bolt 191 and into contact with the distal surface of the spring compression collar 187.

Figure 14:
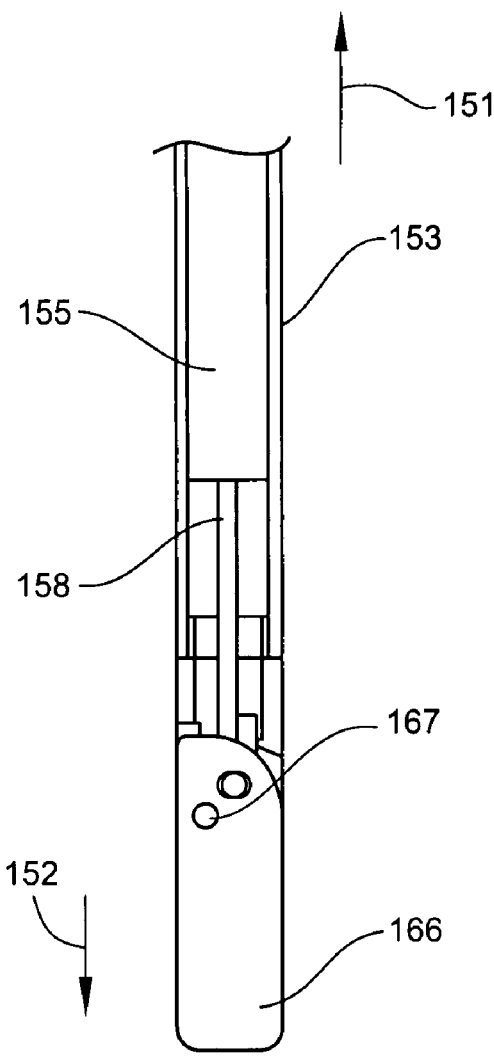
FIG. 14 is a view of the distal end of a rod-shaft-surgical implement assembly in an embodiment of the present invention.
Figure 15:
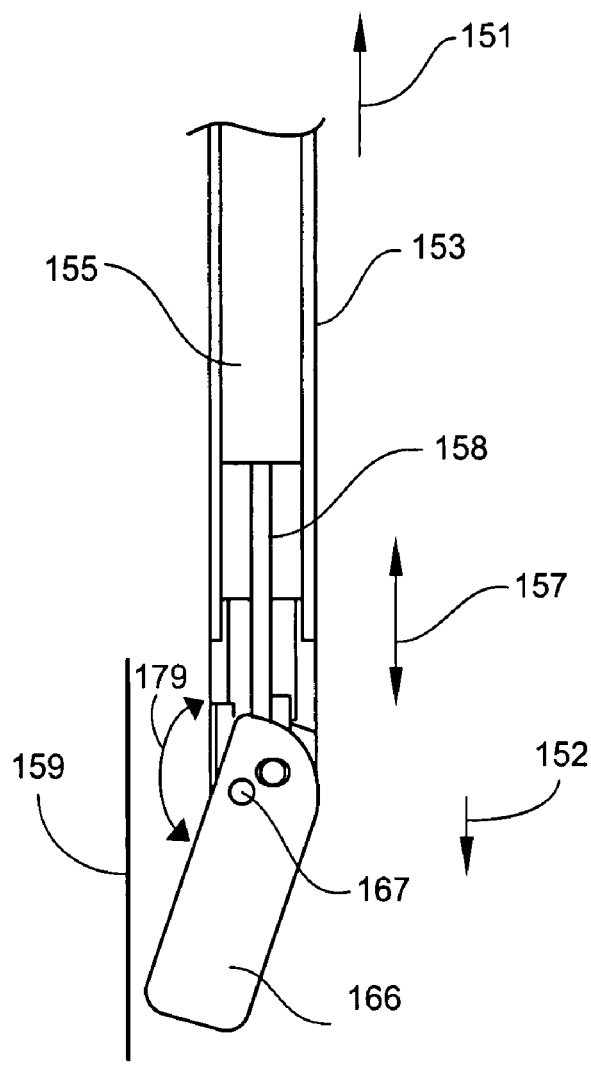
FIG. 15 is a view of the distal end of a rod-shaft-surgical implement assembly shown in FIG. 14, having the surgical implement pivoted away from the longitudinal axis of the shaft and encountering an obstruction.

In an embodiment of the axial load limiting system 186 including a spring 188, the spring 188 can be selected to accept a predetermined axial load before compressing. When the grip portion 194 of the lever 162 is moved in the proximal direction 168 toward the handle 160, the opposite end of the lever 162 in the head 164 of the handle 160 can pivot in the distal direction 169. In this way, the rod 155 can be moved axially in the distal direction 169 so as to pivot the surgical implement 166 about the pivot pin 167 to an angle away from the longitudinal axis 157 of the shaft 153, as shown in FIG. 15. As shown in FIGS. 14 and 15, the distal end 152 of the rod 155 can be connected to the surgical implement 166 with a rod-surgical implement connector 158, for example, a curette "loop." The surgical implement 166 can be connected to the distal end 152 of the hollow shaft 153 about a pivot pin 167. Thus, the rod 155, rod-surgical implement connector 158, and surgical implement 166 assembly can be structurally connected to the hollow shaft 153 at the pivot pin 167. An axial load on the rod 155 less than the axial load limit of the spring 188 can cause the rod 155 to push the rod-surgical implement connector 158 distally and to pivot the surgical implement 166 about the pivot pin 167 to an angle away from the longitudinal axis 157 of the shaft assembly 150. However, when the surgical implement 166 encounters an obstruction 159, such as hard cancellous bone inside a bony structure, for example, a vertebral body, as shown in FIG. 15, movement of the surgical implement 166 away from the shaft 153 can be restricted.

If the surgical implement 166 encounters resistance, as the lever 162 is moved further in the proximal direction 168 toward the handle 160, the axial load pressure placed on the rod 155 may exceed the load tolerance of the rod-surgical implement connector 158 and/or the pivot pin 167. Under excessive axial loads, the rod-surgical implement connector 158 may buckle, the pivot pin 167 may shear, and/or these components may experience other damage and/or otherwise become inoperable. When the axial load placed by the lever 162 on the rod 155 and surgical implement 166 exceeds the predetermined axial load limit of the spring 188, the spring compression collar 187 can be pushed downward in the distal direction 169 (for example, from the position shown in FIG. 12 to the position shown in FIG. 13) to compress the spring 188. That is, when the surgical implement 166 is restricted from movement and further pressure is placed on the lever 162, the increased axial load can cause the rod-surgical implement connector 158 to force the pivot pin 167 and the hollow shaft 153 connected to the pivot pin 167 downward in the distal direction 169. As the shaft 153 moves downward, the spring compression collar 187 connected to the proximal end 151 of the shaft 153 is also moved downward in the distal direction 169 in the handle cavity 176. Downward movement of the spring compression collar 187 can compress the spring 188 so as to transfer the excessive axial load onto the spring 188, thereby providing a buffer to relieve some of the load on the rod-surgical implement connector 158 and the pivot pin 167, as well as the surgical implement 166. As shown in FIG. 13, with such distal movement, the shaft 153 and spring compression collar 187 can be displaced downwardly so as to leave a displacement area 192 above the spring compression collar 187 in the handle cavity 176.

In certain embodiments, the axial load required to compress the spring 188 is less than the force needed to cause components of the surgical tool 10 to become damaged or otherwise inoperable. That is, an axial load that may adversely affect the rod-surgical implement connector 158, pivot pin 167, and/or surgical implement 166 can cause the spring 188 to compress and divert excessive axial load away from those structures and onto the spring 188 before any adverse effect occurs to those structures.

In an embodiment of the surgical tool 10 in which the surgical implement 166 comprises a curette tip, the handle 160 may be rotated with the curette tip 166 at the angle 179 at which the tip 166 meets resistance so as to scrape tissue away to form a larger void at the surgical site, such as inside a vertebral body. When the obstructing tissue 159, such as bone, is scraped away, the curette tip 166 can move under a lower axial load to a greater angle 179 away from the longitudinal axis 157 of the shaft assembly 150. Then, the user can continue to scrape bone away while moving the curette 166 to greater and greater angles 179 away from the longitudinal axis 157 of the shaft 153 without placing an excessive axial load on the surgical tool 10 so as to damage or stop the functioning of the tool 10. In this manner, the handle 160 can be rotated, bone scraped away, and the curette tip 166 further angled without readjusting the position of the lever 162. For example, once the lever 162 is set in a desired position relative to the handle 160, the handle 160 can be rotated to automatically achieve the ultimately desired curette angle 179, for example 90 degrees, relative to the longitudinal axis 157 of the shaft 153 of the device 10 without further lever adjustment.

With the continued scraping away of obstructing tissue 159, the axial load from the lever 162 on the curette tip 166 and compressed spring 188 may become less than the predetermined axial load limit of the spring 188. As a result, the shaft 153 and spring compression collar 187 can move in the proximal direction 168 within the handle cavity 176 so as to allow the spring 188 to decompress. Thus, the shaft 153 and spring compression collar 187 can move, or "float," distally 169 and proximally 168 within the handle cavity 176 as increasing and decreasing axial pressures, respectively, are placed on the rod 155, rod-surgical implement connector 158, and connector-surgical implement-pivot pin assembly (or surgical implement assembly). Thus, some embodiments of the present invention can provide a configuration of the axial load limiting system 186 that can serve as a safety mechanism for protecting the integrity of components of the surgical tool 10 when under increased axial loads. Certain embodiments of the axial load limiting system 186 may allow the user to operate the surgical tool 10 under any axial loading condition without concern that the maximum force limits of the tool 10 will be exceeded.

Figure 16:
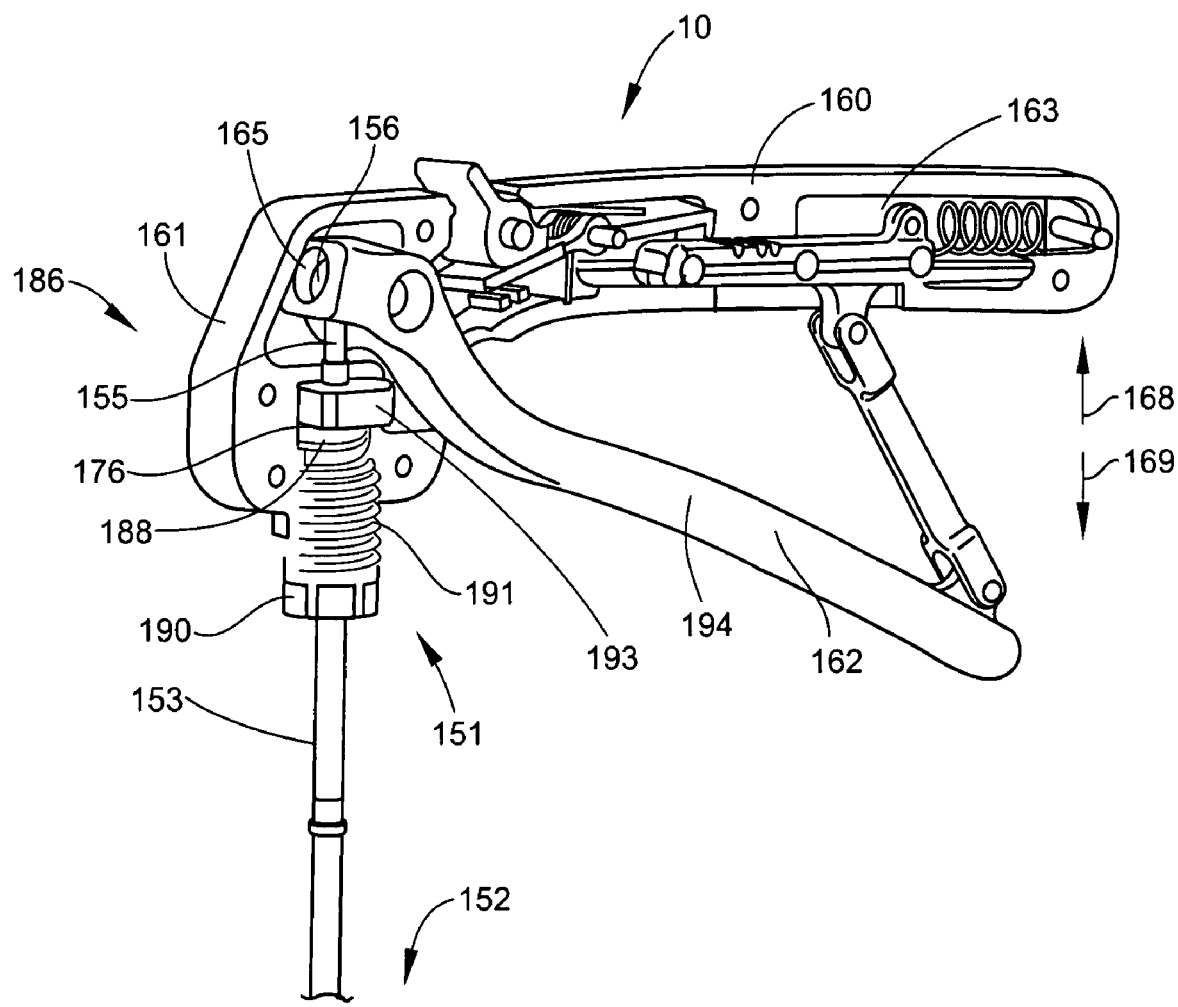
FIG. 16 is a view of a surgical tool having another embodiment of an axial load limiting system of the present invention.

Some embodiments of the axial load limiting system 186 can comprise various other components and configurations. For example, as shown in FIG. 16, the surgical tool 10 can include the axial load limiting system 186 comprising a hub 193. The hub 193 can be integrally formed with or fixedly connected to the hollow shaft 153 near the proximal end 151 of the hollow shaft 153. The hub 193 can be keyed to a space, such as the cavity 176, in the handle housing 161 such that as the handle 160 is rotated, the shaft assembly 150 rotates with the handle 160. That is, the hub 193 fixed to the hollow shaft 153 and to the handle 160 can prevent rotation of the shaft 153 independent of rotation of the handle 160. In certain embodiments, the hub 193 can serve as a means for compressing the biasing mechanism. That is, the hub 193 can function as a spring compression hub 193, such that when the axial load exceeds the predetermined axial load limit of the spring 188, the shaft 153 and the hub 193 can be moved downwardly in the distal direction 169 within the handle cavity 176. The spring compression hub 193 can compress the spring 188 to absorb the excessive axial load and thereby buffer the rod-surgical implement connector 158, pivot pin 167, and/or surgical implement 166 from any adverse effects from the increased axial load.

In some embodiments, the surgical tool 10 may include both an embodiment of the axial load limiting system 186 and an embodiment of the torque limiting system 170. Such an embodiment may include the torque limiting device 170, for example, as shown in and described relative to FIGS. 8-11.

For example, in the embodiment shown in FIGS. 10, 11, 17, and 18, the torque limiting device 170 may be attached to the handle 160 and to the shaft assembly 150, so that rotation of the handle 160 causes rotation of the shaft assembly 150 and rod 155, and, in turn, rotation of the surgical implement 166. The torque limiting device 170 can include a first torque limiting element releasably engageable with a second torque limiting element. The torque limiting device 170 can comprise a ball plunger (not shown) having a ball, or engaging end, and the ball engaging receptacle, such as the ball detent collar 154, having a detent 172, in its outer surface. The ball plunger and engaging ball may be similar to the ball plunger 128 and ball 130 shown in FIG. 3. The ball detent collar 154 can be fixed to the proximal end 151 of the shaft 153. The detent 172 in the ball detent collar 154 may be configured to receive and engage the ball of the ball plunger. The engaging ball may be various shapes that allow for engagement and disengagement with the ball detent 172.

The ball plunger and attached engaging ball can be housed in a ball plunger housing 173. The ball plunger housing 173 can be seated in a depression in the handle housing 161 and can be aligned perpendicularly with the ball detent collar 154 such that the engaging ball is engageable with the detent 172 in the ball detent collar 154. The ball plunger housing 173 may comprise a hollow cylinder, within which the ball plunger and engaging ball can slide at least partially along the longitudinal axis of the ball plunger housing 173. A biasing mechanism (not shown), for example, a compression spring, can be positioned between the outer end 174 of the ball plunger housing 173 and the ball plunger so as to bias the ball plunger longitudinally in the ball plunger housing 173 toward the ball detent 172 in the ball detent collar 154.

The engaging ball and the detent 172 in the ball detent collar 154 may be matingly configured such that the ball can engage the detent 172 so that the ball detent collar 154 and attached shaft 153 can be rotated when the handle 160 is rotated. A frictional engagement interface, or torque translation interface, between the engaging ball and the ball detent 172 can allow rotational force applied to handle 160 and the ball plunger to be translated to the shaft 153. When the ball and ball detent 172 are engaged, that is, when the ball and ball detent 172 are rotationally aligned and the ball is positioned within the detent 172, rotation of the handle 160 can cause rotation of the surgical implement 166.

When a user applies pressure to rotate the handle 160 beyond a predetermined torque limit, the ball plunger may be compressed and the engaging ball rises out of engagement with the ball detent 172 to a disengaged position. That is, the engaging ball and the ball detent 172 are releasably engageable. When the ball and ball detent 172 are disengaged, rotation of the handle 160 no longer causes a rotation of the surgical implement 166. When the handle 160 is rotated while the engaging ball is disengaged from the ball detent 172, the handle 160 rotates about the rod 153 by means of the ball joint receptacle 165 in the lever 162 rotating about the ball joint 156 of the rod 153. As such, the handle 160 is disengaged from the shaft assembly 150, and breaking of the surgical tool 10 from too great a torque can be avoided. When the engaging ball becomes disengaged from the ball detent 172 on the shaft 153, the handle 160 can be freely rotated to reposition the ball plunger, and engaging ball, back into the ball detent 172 to re-engage the handle 160 with the shaft assembly 150. In addition to avoiding breaking of the surgical tool 10, use of the tool can be readily resumed without removing the tool 10 to repair or reset it for further use.

Figure 17:
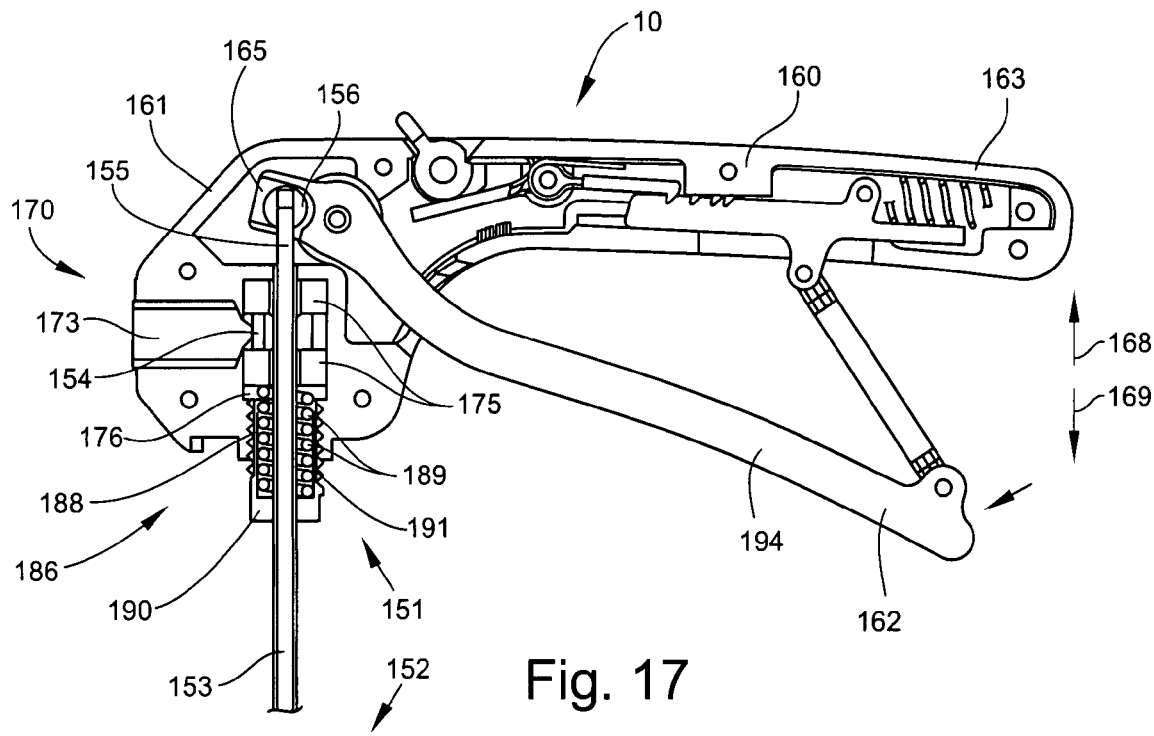
FIG. 17 is a view of a surgical tool having an axial load limiting system and a torque limiting system in another embodiment of the present invention.
Figure 18:
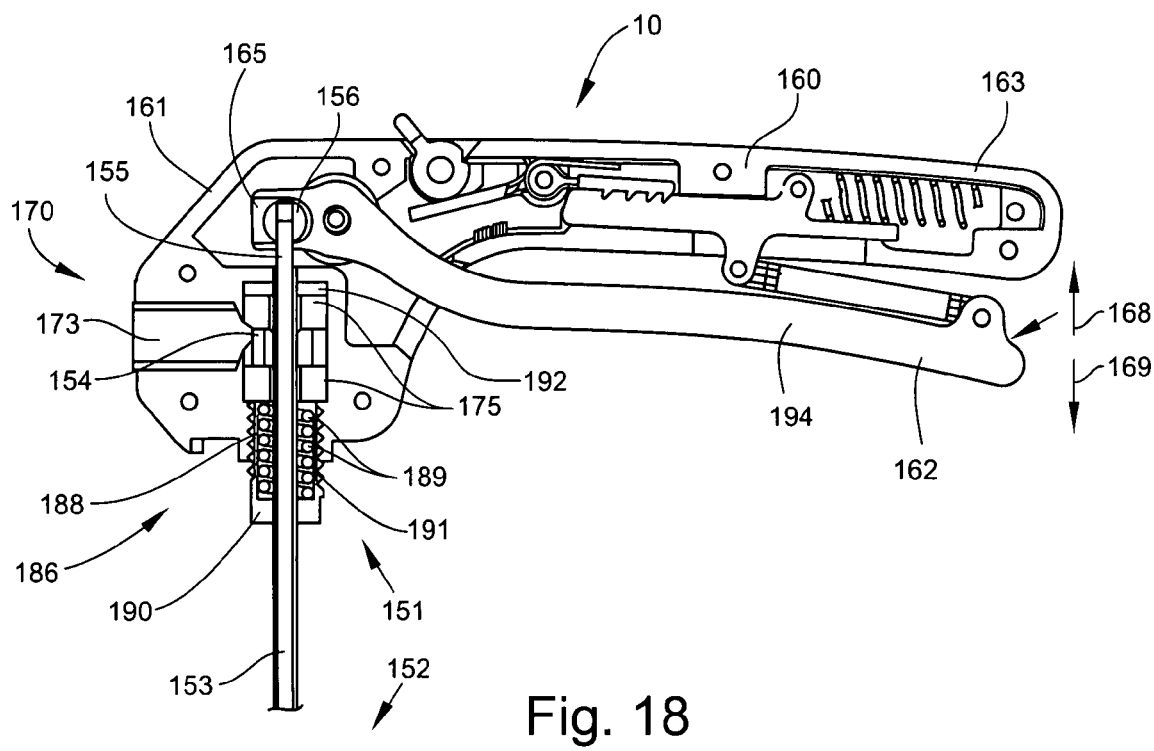
FIG. 18 is a view of the embodiment of the surgical tool shown in FIG. 17, showing the lever moved to a position adjacent the handle and displacement of the spring compression collar and spring in the distal direction.

As shown in FIGS. 17 and 18, the ball detent collar 154 may be in rotatable contact with the thrust bearing 175 adjacent the proximal 151 surface, or top, of the collar 154 and with another thrust bearing 175 adjacent the distal 152 surface, or bottom, of the collar 154. As shown in this embodiment, each of the thrust bearings 175 can be housed in the cavity 176 in the handle housing 161. Ball bearings (not shown) are located at the interface between the thrust bearings 175 and the ball detent collar 154. The thrust bearings 175 can help reduce friction between the ball detent collar 154 and the handle 160 when the ball plunger is disengaged from the ball detent 172 and the handle 160 is rotated freely about the shaft assembly 150 after a predetermined torque limit is surpassed.

Figure 12:
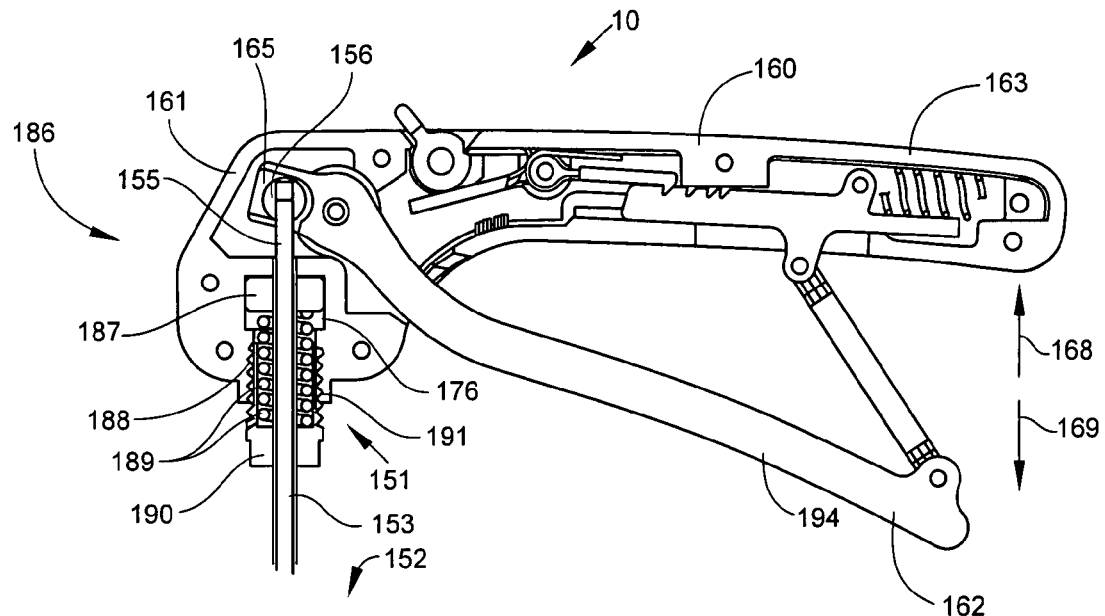
FIG. 12 is a view of a surgical tool having an axial load limiting system in another embodiment of the present invention.
Figure 13:
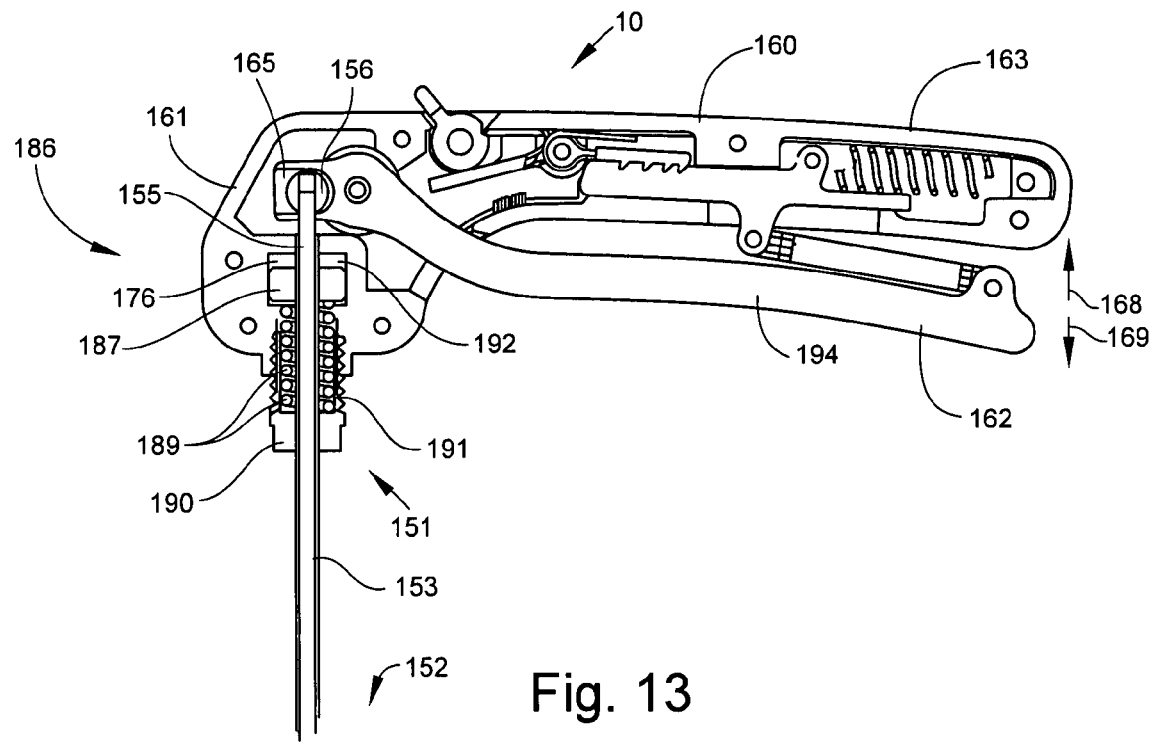
FIG. 13 is a view of the embodiment of the surgical tool shown in FIG. 12, showing the lever moved to a position adjacent the handle and displacement of the spring compression collar and spring in the distal direction.

As shown in the embodiment in FIGS. 17 and 18, the surgical tool 10 can include the axial load limiting system 186 similar to the embodiment shown in and described relative to FIGS. 12 and 13. In such an embodiment, the hollow, threaded bolt 191 having a spring 188 or other biasing mechanism inside the bolt 191 can be slid over the hollow shaft 153 and the bolt 191 threaded into the threads 189 of the handle cavity 176 to a preset point. The lock nut 190 can then be slid over the hollow shaft 153 and fastened into position about the shaft 153 in contact with the bottom surface of the threaded bolt 191 so as to maintain the bolt 191 in a constant position inside the handle housing 161. The spring 188 can be set to remain in stationary position until a predetermined axial load threshold on the spring 188 is reached. In this embodiment, rather than the spring compression collar 187 being attached to the hollow shaft 153, the thrust bearings 175 can be fixedly attached to the exterior of the shaft 153. The ball detent collar 154 and the thrust bearings 175 can be configured to move in a downward and upward axial motion within the handle cavity 176 with respect to the longitudinal axis 157 of the hollow shaft 153. The spring 188 can be configured to extend upward beyond the top of the hollow bolt 191 and into contact with the distal 152 surface of the lower thrust bearing 175.

The spring 188 can be configured to accept a predetermined axial load before compressing. When the grip portion 194 of the lever 162 is moved in the proximal direction 168 toward the handle 160, the opposite end of the lever 162 in the head 164 of the handle 160 can pivot in the distal direction 169. In this way, the rod 155 can be moved axially in the distal direction 169 so as to pivot the surgical implement 166 about the pivot pin 167 to an angle 179 away from the longitudinal axis 157 of the shaft 153, as shown in FIG. 15. When the surgical implement 166 encounters an obstruction 159, such as hard bone inside a bony structure, for example, a vertebral body, as shown in FIG. 15, movement of the surgical implement 166 away from the shaft 153 can be restricted. Further movement of the lever 162 in the proximal direction 168 toward the handle may place an axial load pressure on the rod 155 that exceeds the load tolerance of the rod-surgical implement connector 158 and/or the pivot pin 167.

When the axial load placed by the lever 162 on the rod 155 and surgical implement 166 exceeds the predetermined axial load limit of the spring 188, the ball detent collar 154 and the thrust bearings 175 can be pushed downward in the distal direction 169 (for example, from the position shown in FIG. 17 to the position shown in FIG. 18) to compress the spring 188. In such an embodiment, the height of the ball detent collar 154 and the ball detent 172 can be sufficient to allow downward and upward movement of the ball detent collar 154 and the thrust bearings 175 relative to the ball plunger so as to maintain the engaging ball engaged with the detent 172 during such downward and upward movement.

When the surgical implement 166 is restricted from movement and further pressure is placed on the lever 162, the increased axial load can cause the rod-surgical implement connector 158 to force the pivot pin 167 and the hollow shaft 153 connected to the pivot pin 167 downward in the distal direction 169. As the shaft 153 moves downward, the ball detent collar 154 and the thrust bearings 175 connected to the proximal end 151 of the shaft 153 are also moved downward in the distal direction 169 in the handle cavity 176. Downward movement of the lower thrust bearing 175 can compress the spring 188 so as to transfer the excessive axial load onto the spring 188, thereby providing a buffer to relieve some of the load on the rod-surgical implement connector 158 and the pivot pin 167, as well as the surgical implement 166. As shown in FIG. 18, with such distal movement, the shaft 153, ball detent collar 154, and thrust bearings 175 can be displaced downwardly so as to leave the displacement area 192 above the upper thrust bearing 175 in the handle cavity 176. Thus, such an embodiment of the present invention can provide, in combination with the torque limiting system 170, a configuration of the axial load limiting system 186 that can serve as a safety mechanism for protecting the integrity of components of the surgical tool 10 when under increased axial loads.

Figure 19:
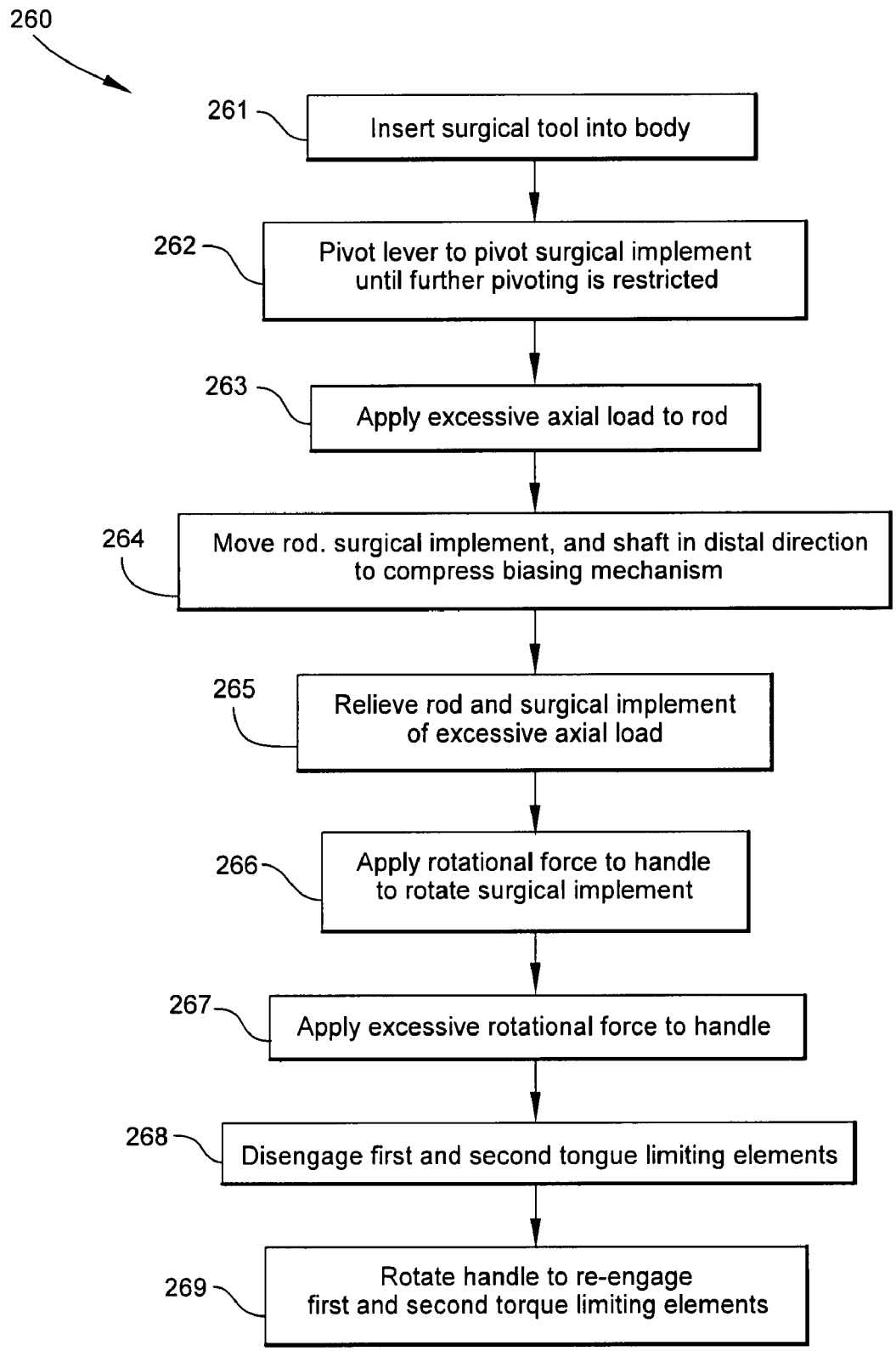
FIG. 19 is a block diagram representation of an embodiment of a method of the present invention.
Figure 20:
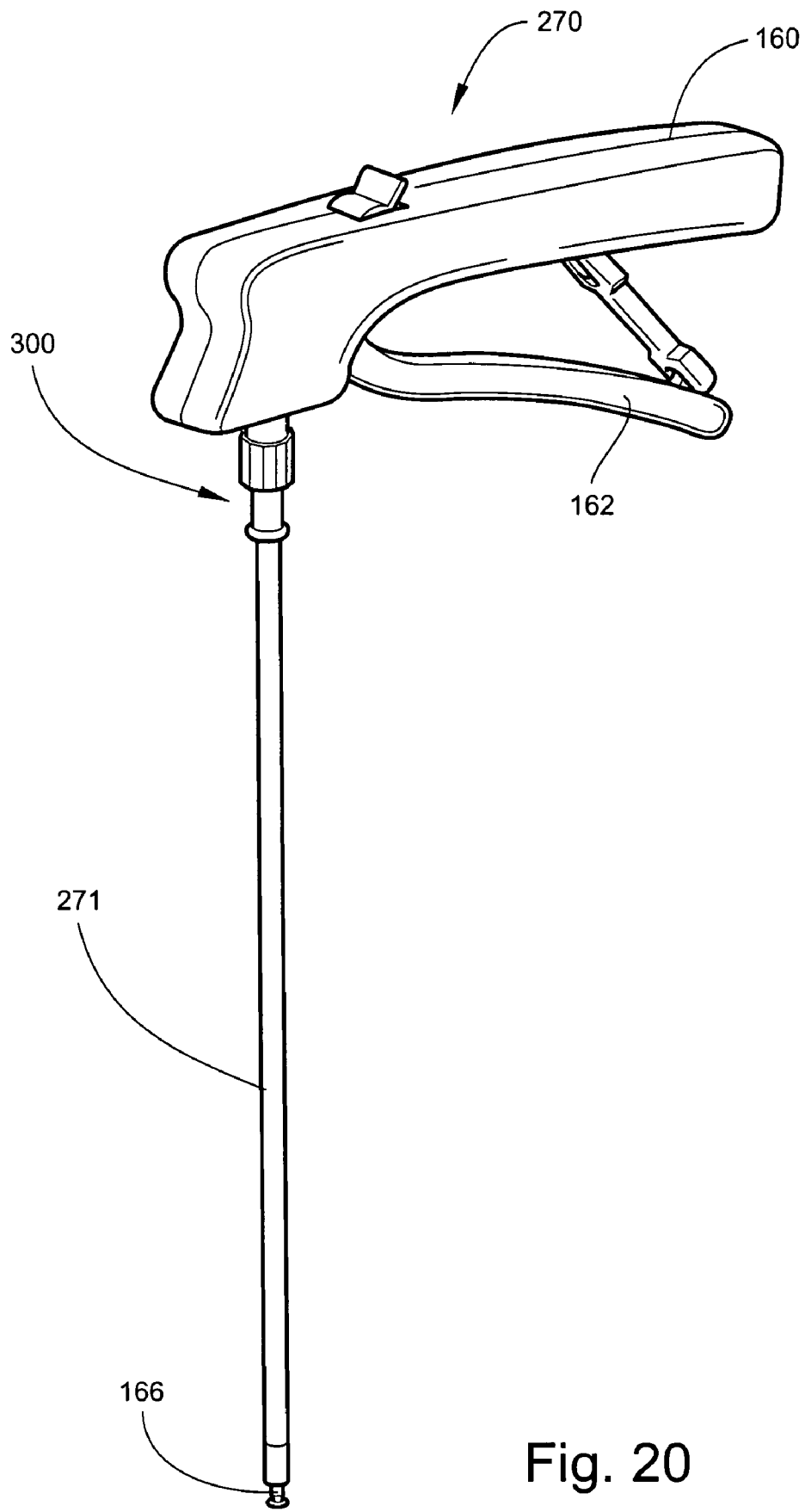
FIG. 20 is a perspective view of a surgical tool having interchangeable shaft assembly and coupler assembly components shown assembled in an embodiment of the present invention.
Figure 21:
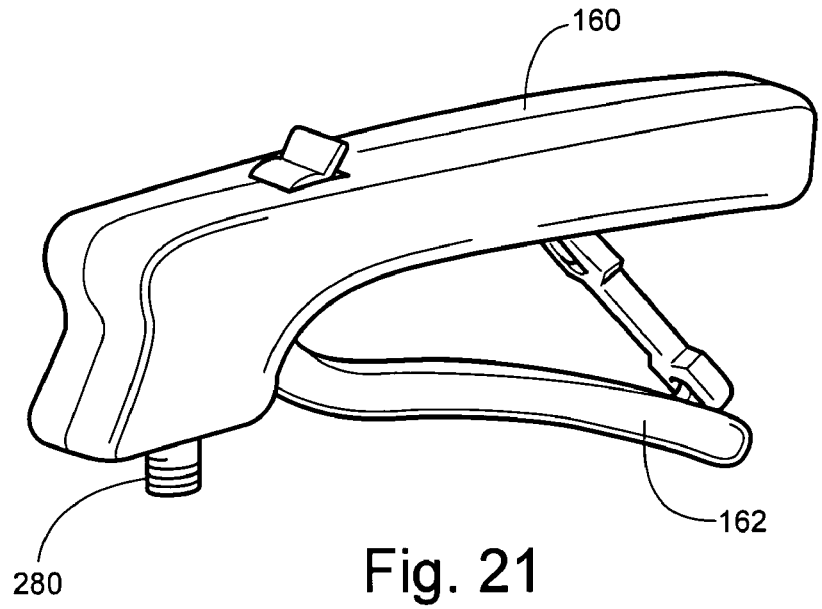
FIG. 21 is a view of the embodiment of the surgical tool handle shown in FIG. 20, showing a portion of the docking assembly.

Some embodiments of the present invention can include a method 260 for using the axial load limiting system 186, as described herein. Referring now to FIG. 19, the illustrated embodiment of the method 260 comprises inserting (261) the surgical tool 10 into a body, the surgical tool 10 having the axial load limiting system 186. The axial load limiting system 186 can include the handle 160 having the lever 162 pivotably connected to the handle 160, the hollow shaft 153 slidably attached to the handle 160, and the rod 155 operably connected on the proximal end 151 to the lever 162 and movable axially inside the shaft 153. The surgical implement 166 can be connected to the distal end 152 of the rod 155 and pivotably connected to the distal end 152 of the shaft 153. The axial load limiting system 186 can further include a biasing mechanism adapted to be compressed within the cavity 176 in the handle 160 by an axial load in excess of a predetermined axial load. The surgical implement 166, such as a curette, can be positioned at a desired interior body region, for example, inside a vertebral body.

The lever 162 can be pivoted (262) relative to the handle 160 to pivot the surgical implement 166. When further pivoting of the surgical implement 166 is restricted due to an obstruction 159, such as hard tissue, an excessive axial load can be applied (263) to the rod 155. The excessive axial load can cause the rod 155, surgical implement 166, and shaft 153 to be moved (264) in the distal direction 169 so as to compress the biasing mechanism. In this manner, the excessive axial load can be absorbed by the biasing mechanism, thereby relieving (265) the rod 155, surgical implement 166, and other attached structures of the surgical tool 10 of the excessive axial load. In an embodiment of such a method 260 in which the surgical implement 166 comprises a curette tip, the handle 160 may be rotated so as to rotate the curette tip 166 and scrape tissue at a surgical site.

Some embodiments of the present invention can include the method 260 for using a torque limiting system, for example, the torque limiting system 170 as shown in FIGS. 9 and 17-18, in combination with the axial load limiting system 186. For example, the surgical tool 10 can further include a torque limiting system comprising a first torque limiting element connected to the handle 160, and a second torque limiting element operably connected to the shaft 153 and releasably engageable with the first torque limiting element. The method 260 can include applying (266) a first rotational force to the handle 160 to rotate the shaft 153, rod 155, and surgical implement 166. A second rotational force that exceeds a predetermined torque limit can be applied (267) to the handle 160, for example, when the surgical implement 166 encounters the obstruction 159. When the rotational force that exceeds a predetermined torque limit is applied to the handle, the first torque limiting element can become disengaged (268) from the second torque limiting element such that the handle 160 rotates without rotation of the shaft 153, rod 155, and surgical implement 166.

After the first and second torque limiting elements have become disengaged (268), the method 260 may further include rotating (269) the handle to re-engage the first torque limiting element with the second torque limiting element. Once the torque limiting elements have been re-engaged (269), the handle 160 can again be rotated (266) to rotate the shaft 153, rod 155, and surgical implement 166.

In another aspect of the present invention, a surgical device, or tool, can include interchangeable components. For example, as shown in FIGS. 20-28, some embodiments of the surgical device 270 having interchangeable components can include the handle 160, a docking assembly 280, a shaft assembly 290, and a coupler assembly 300.

As shown in FIGS. 21, 22A, 22B, 27, and 28, the docking assembly 280 can include a docking rod 281 having a ball joint 156 attached at the distal end 151 of the rod 281. The lever 162 can be pivotably attached to the head of the handle 160 and in operative connection with the ball joint 156 of the docking rod 281. The handle 160 and lever 162 can be attached about the ball joint 156 with the ball joint receptacle 165. The docking rod 281 can be axially slidable within a docking assembly housing 286 and a portion of a detachable shaft 271 to operate the surgical implement 116 at the distal end 152 of a shaft rod 291.

Figures 22A, 22B:
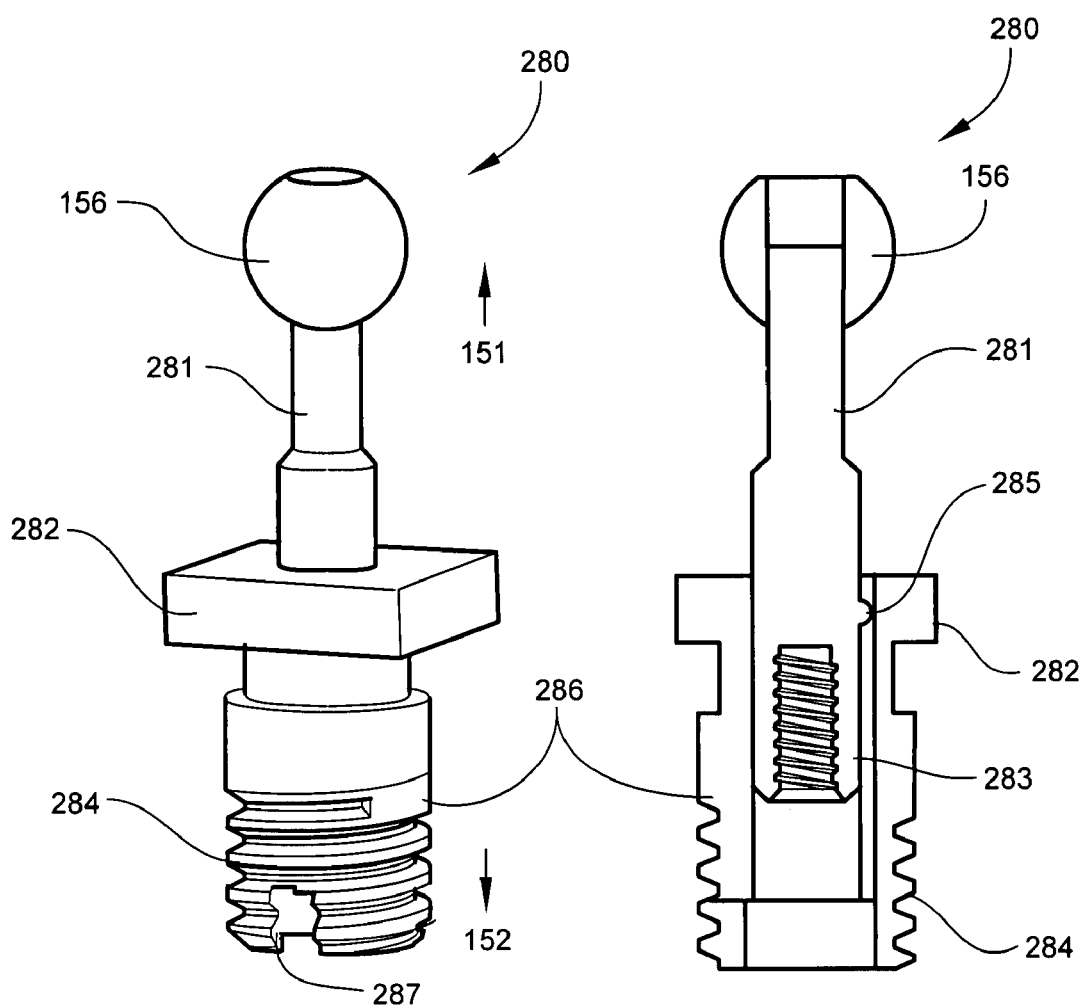
FIG. 22A is a view of a docking assembly in an embodiment of the present invention.
FIG. 22B is a cross-sectional view of the docking assembly shown in FIG. 22A.
Figure 27:
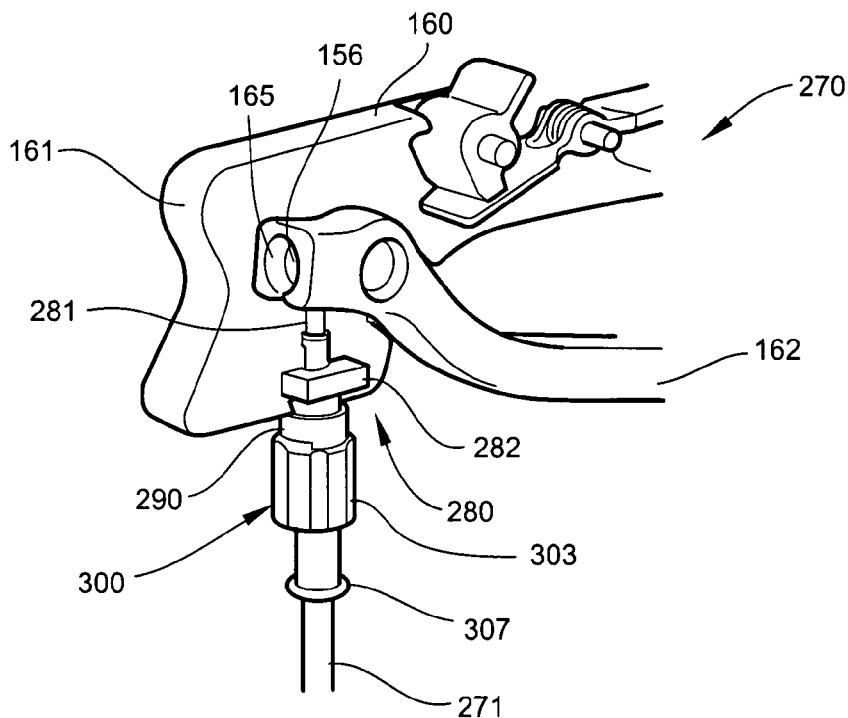
FIG. 27 is a view of the embodiment of the surgical tool handle shown in FIG. 20, shown partially disassembled to reveal the assembly of the docking assembly, shaft assembly, and coupler assembly.

The docking assembly 280 can include a flange 282, such as a rectangular block as shown in FIGS. 22A and 27, attached to or integrally formed with the docking assembly 280, configured to fit matingly within the cavity 176 of the handle 160. The flange 282 can secure the docking assembly 280 within the handle 160 such that the outer components of the docking assembly 280 cannot move relative to the handle 160. In certain embodiments, the docking assembly 280 can include a projection 285 extending at substantially a 90 degree angle from the docking rod 281 near the flange 282. The projection 285 can contact a portion of the internal surface of the docking assembly housing 286 so that the docking rod 281 can be prevented from rotating within the docking assembly housing 286. As a result, the docking rod 281 may be configured to move only vertically, or axially, within the docking assembly housing 286 and the detachable shaft 271.

The distal end 152 of the docking rod 281 can include internal threads 283 for receiving a matingly threaded rod 291 in the shaft assembly 290, described later. The docking assembly housing 286 can include external threads 284 formed about the distal end 152 of the housing 286. The external threads 284 of the docking assembly housing 286 can be mated with a threaded cap 303 in the coupler assembly 300, described later. In certain embodiments, the docking assembly housing 286 can include a thread notch 287 in the external threads 284 designed for mating with a thread key 301, described later, in the coupler assembly 300.

Figure 23:
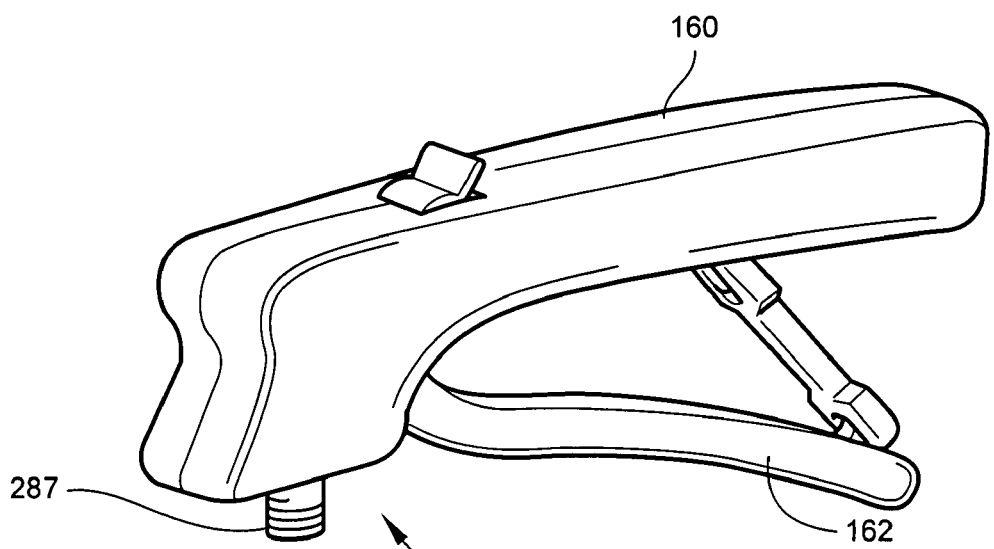
FIG. 23 is a view of the embodiment of the surgical tool handle shown in FIG. 20, showing a portion of the docking assembly and a portion of the shaft assembly.
Figure 24:
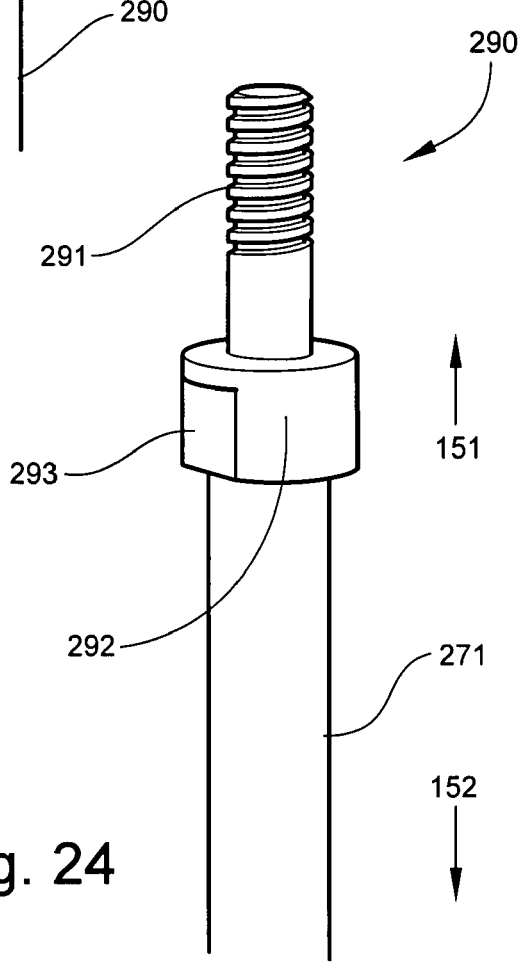
FIG. 24 is a close-up view of the shaft assembly shown in the embodiment in FIG. 23.
Figure 25:
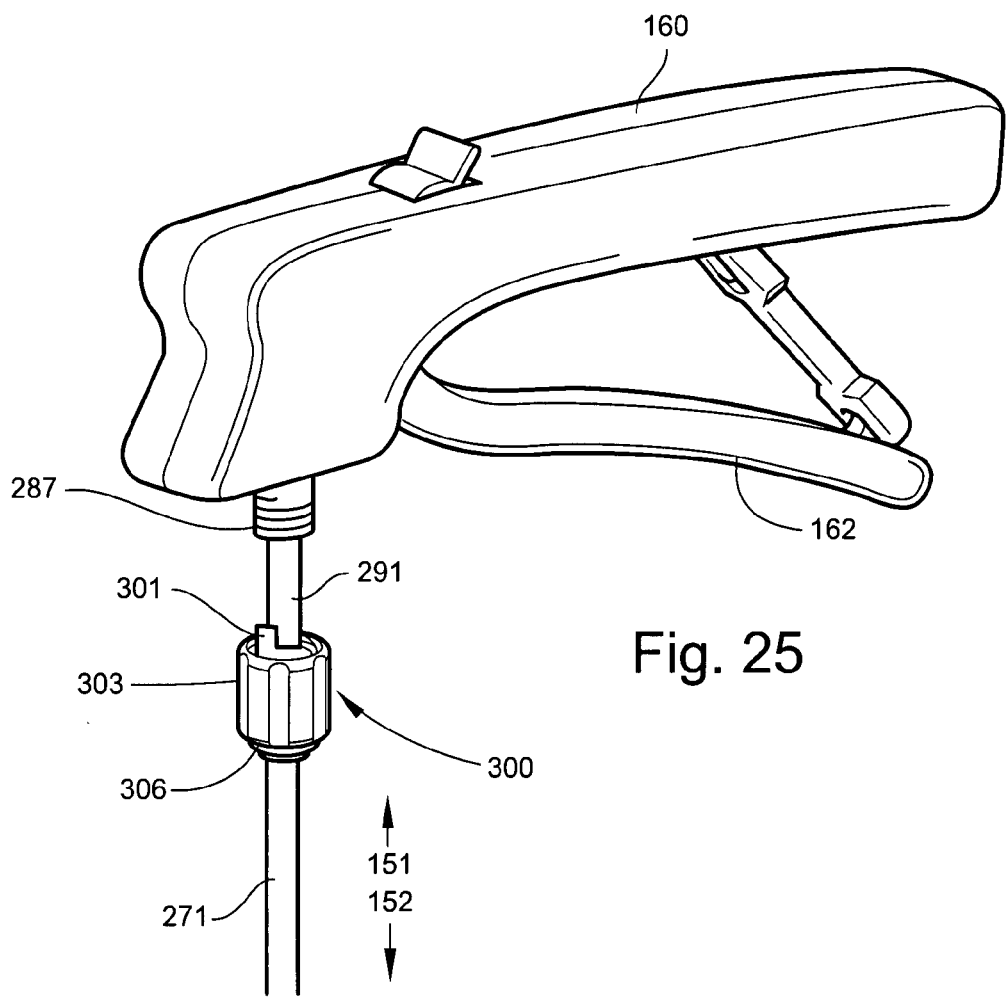
FIG. 25 is a view of the embodiment of the surgical tool handle shown in FIG. 20, showing the shaft assembly abutting the docking assembly and the coupler assembly positioned about the detachable shaft.
Figures 26A, 26B:
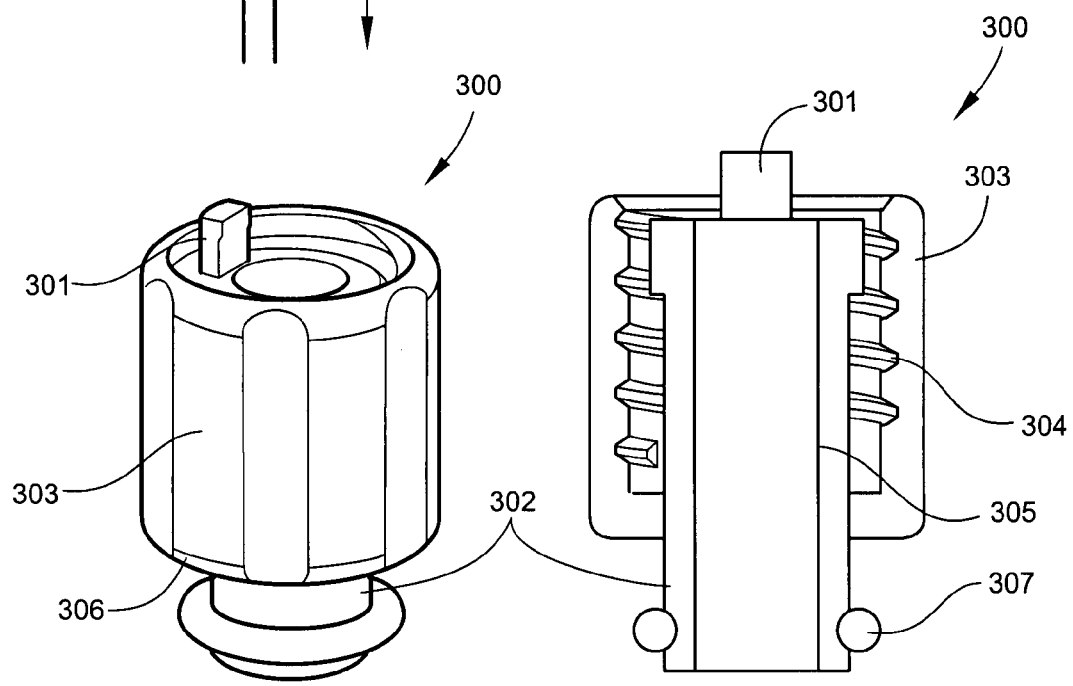
FIG. 26A is a view of a coupler assembly in an embodiment of the present invention.
FIG. 26B is a cross-sectional view of the coupler assembly in FIG. 26A.
Figure 28:
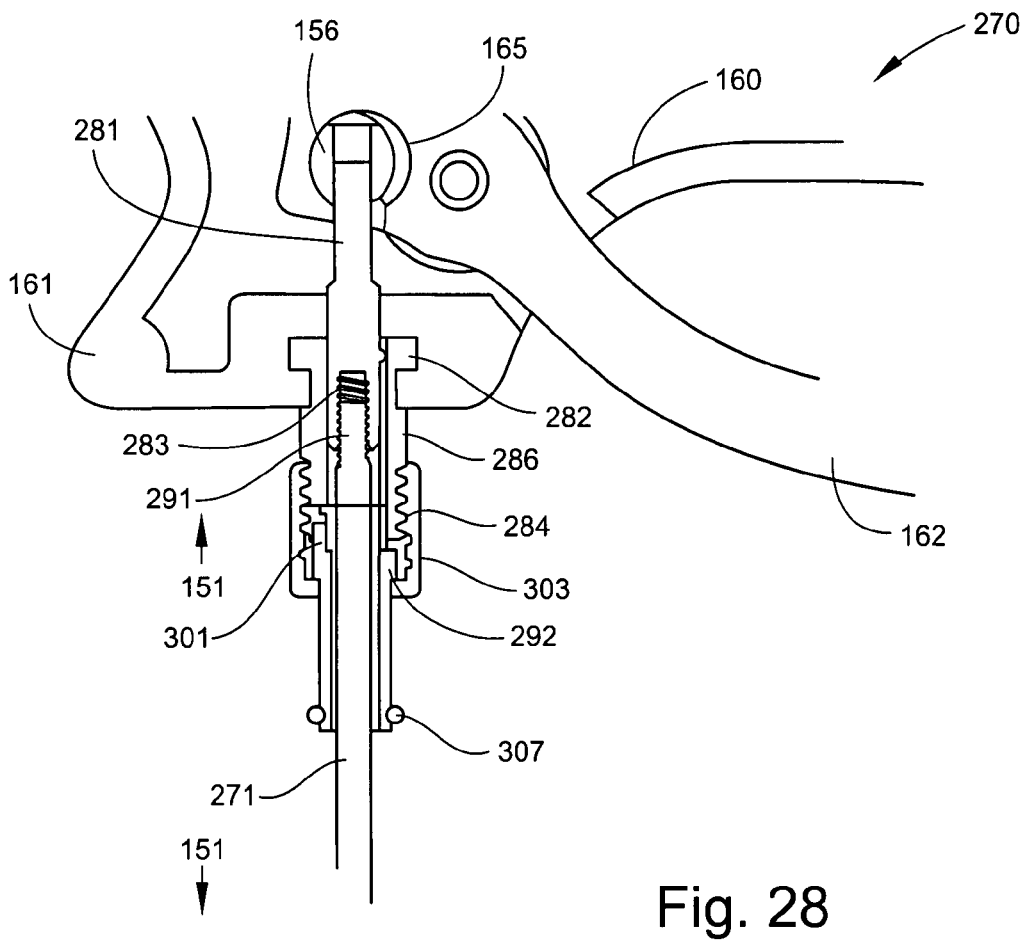
FIG. 28 is a cross-sectional view of the embodiment of the surgical tool handle shown in FIG. 20, and of the docking assembly, shaft assembly, and coupler assembly when assembled together.

As shown in FIGS. 23, 24, and 28, the shaft assembly 290 of the surgical device 270 can include the shaft 271 that can be attached to and unattached from the docking assembly 280. The shaft assembly 290 can include the threaded shaft rod 291 that can slide axially within the detachable shaft 271. The surgical implement 166 can be operably attached to the distal end 152 of the threaded shaft rod 291. The proximal end 151 of the shaft rod 291 can include threads configured to matingly thread into the internal threads 283 of the docking rod 281 in the docking assembly 280. The proximal end 152 of the detachable shaft 271 can have a shaft shoulder 292 fixedly attached or integrally formed with the exterior of the shaft 271. The shaft shoulder 292 can be designed to abut against the distal 152 surface of the docking assembly 280, as shown in FIGS. 27 and 28, so as to prevent the detachable shaft 271 from further insertion into the docking assembly 280. In certain embodiments, the shaft shoulder 292 can include a shoulder flat 293, or a flattened portion of the shaft shoulder 292. The shoulder flat 293 can be aligned with the thread notch 287 in the docking assembly 280 and with the thread key 301 in the coupler assembly 300.

As shown in FIGS. 25, 26A, 26B, 27, and 28, the coupler assembly 300 of the surgical device 270 can include a sleeve 302 having an internal diameter 305 sufficient to fit about the exterior surface of the detachable shaft 271. The coupler assembly 300 can include the cap 303 that can slide axially about the coupler assembly sleeve 302. The cap 303 can have internal threads 304 designed to mate with the external threads 284 on the docking assembly housing 286. When the shaft shoulder 292 of the detachable shaft 271 is abutted against the distal end 152 of the docking assembly 280, the cap 303 can be slid upward in the proximal direction 151 and threaded about the external threads 284 of the docking assembly housing 286. When threaded into position on the external threads 284 of the docking assembly 280, the distal edge 306 of the coupler cap 303 can fit tightly against the distal surface of the shaft shoulder 292. In this manner, the docking assembly 280 and the shaft assembly 290 can be releasably secured together during use. A cap retention mechanism 307, such as an O-ring, can be positioned near the distal end 152 of the coupler assembly sleeve 302 so that the coupler cap 303 can be retained on the sleeve 302 for ease of use.

In certain embodiments, the thread key 301 can be attached to, or integrally formed with, the proximal surface of the coupler assembly sleeve 302. When the coupler assembly 300 is placed near the shaft shoulder 292 of the shaft assembly 290, the coupler assembly 300 can be rotated so that the thread key 301 is aligned with and placed across and against the shoulder flat 293 in the shaft shoulder 292. The thread key 301 can be also aligned with and inserted into the thread notch 287 in the external threads 284 of the docking assembly housing 286. The alignment and locking interaction between the thread key 301, the shoulder flat 293, and the thread notch 287 can prevent the shaft assembly 290 from rotating during use.

Thus, some embodiments of the present invention can allow a surgeon to quickly interchange multiple configurations of the shaft 271 and the surgical implement 166 with the surgical device handle 160. In certain embodiments, various configurations of the shaft 271 and the surgical implement 166 can be interchanged with the surgical device handle 160 without the use of any tools. Such embodiments of the surgical device 270 that allow multiple configurations of the shaft 271 and/or the surgical implement 166 to be assembled with and disassembled from the surgical device handle 160 can reduce inventory needs for handles and thus decrease costs.

Some embodiments of the present invention can provide a kit comprising the surgical device 270 and interchangeable components. For example, in an embodiment of a kit, the handle 160 can be packaged with a plurality of detachable shafts 271 and surgical implements 166 having various configurations. In this way, a surgeon can have a choice of shafts 271 and surgical implements 166 readily available during a particular surgical procedure. Packaging a plurality of shafts 271 and surgical implements 166 having various configurations with a single surgical tool handle 160 can be more cost-effective than packaging each detachable shaft 271 and/or surgical implement 166 separately from the handle 160. In addition, an embodiment of a kit may include different types of surgical implements 166, for example, a curette, a drill, and/or a retractor device, etc., that can be quickly attached to the surgical tool handle 160.

Detachable surgical device shafts 271 and surgical implements 166 attachable to the handle 160 can have various configurations. For example, the detachable shaft 271 can have various dimensions, be made of various materials, and/or have different flexibilities. The surgical implement 166, such as a curette, can have various dimensions and/or shapes, be made of various materials, connect to the surgical device 270 in various ways, and/or have various modes of operation.

Some embodiments of the present invention can include a method 400 for using the surgical device 270 having interchangeable components, as described herein. As shown in the embodiment illustrated in FIG. 29, the method 400 can comprise providing (401) the surgical device handle 160 having the lever 162 pivotably connected thereto, and the docking assembly 280 secured to the handle 160. The docking assembly 280 can have the docking rod 281 operably attached to the lever 162 and axially slidable within the docking assembly 280. The method can further include providing (402) a plurality of shaft assemblies 290, at least one coupler assembly 300, and at least one surgical implement 166. Each shaft assembly 290 can comprise a configuration of the shaft rod 291 axially slidable within the detachable shaft 271 and removably attachable to the docking rod 281. The coupler assembly 300 can be adapted to releasably secure each shaft assembly 290 to the docking assembly 280. The surgical implement 166 can be attached to the distal end 152 of the shaft rod 291 and operable with the lever 162. The method can further include selecting (403) a first of the plurality of shaft assemblies 271. The shaft rod 291 of the first shaft assembly 290 can be removably attached (404) to the docking rod 281. Then, the first shaft assembly 290 can be releasably secured (405) to the docking assembly 280 with the coupler assembly 300. When the first shaft assembly 20 is secured to the docking assembly 280, the handle 160 and lever 162 can be manipulated (406) to operate the surgical implement 166 connected to the first shaft assembly 290.

In some embodiments of such a method, a second of the plurality of shaft assemblies 290 can be selected (407). The first shaft assembly 290 can be released (408) from the docking assembly 280, and the shaft rod 291 of the first shaft assembly 290 can be removed (409) from the docking rod 281. The shaft rod 291 of the second shaft assembly 290 can then be removably attached (410) to the docking rod 281. The second shaft assembly 290 can be releasably secured (411) to the docking assembly 280 with the coupler assembly 300. And, the handle 160 and lever 162 can be manipulated (412) to operate the second shaft assembly surgical implement 166.

In some embodiments, the docking rod 281 can have internal threads 283 in the distal end 152 of the docking rod 281, and the shaft rod 291 of each shaft assembly 290 can have external threads 284 on the proximal end 151 of the shaft rod 291. Removably attaching (404, 410) the shaft rod 291 to the docking rod 281 can thus include threading the shaft rod 291 into the internal threads 283 of the docking rod 281.

In some embodiments, the docking assembly 280 can have external threads 284 on the distal end 152 of the docking assembly 280, and the coupler assembly 300 can include a coupler cap 303 having internal threads 304. Releasably securing (405, 411) the first shaft assembly 290 to the docking assembly 280 with the coupler assembly 300 can thus include threading the coupler cap 303 onto the external threads 284 of the docking assembly 280.

In some embodiments, the docking assembly external threads 284 can include a thread notch 287, the detachable shaft 271 of each shaft assembly 290 can include a shaft shoulder 292 attached to the proximal end 151 of the detachable shaft 271, the shaft shoulder 292 can have a shoulder flat 293, and the coupler assembly 300 can include the thread key 301 extending from the proximal end 151 of the coupler assembly 300. As such, releasably securing (405, 411) the shaft assembly 290 to the docking assembly 280 with the coupler assembly 300 can include aligning the thread key 301 with the shoulder shaft 292 and inserting the thread key 301 into the thread notch 287 so as to prevent the shaft assembly 290 from rotating.

In some embodiments of the present invention, the surgical device 10 can comprise a handle, for example, the handle 160, and an elongated member such as shaft 153 extending from the handle 160. The elongated member 153 can be configured such that the distal end 152 of the elongated member 153 can be percutaneously placed into a tissue in a patient's body. The surgical device 10 can include a torque limiting mechanism, such as torque limiting mechanism 170, that couples the proximal portion 151 of the elongated member 153 to the handle 160. The elongated member 153 can be capable of axial rotation about the longitudinal axis 157 of the elongated member 153 such that the torque limiting mechanism 170 can disallow axial rotation of the elongated member 153 when a torque on the elongated member 153 is greater than a predetermined amount.

In certain embodiments, the torque limiting mechanism 170 may further include a ball bearing (not shown) biased into engagement with the elongated member 153 and capable of disengagement from the elongated member 153. When a torque on the elongated member 153 is greater than a predetermined amount, the ball bearing can be disengaged from the elongate member 153 so as to avoid placing too great a torque on the elongated member 153. After becoming disengaged, the ball bearing may be re-engaged with the elongated member 153. In particular embodiments, the ball bearing can be configured to be engaged with and disengaged from the elongated member 153 in a direction substantially perpendicular to a longitudinal axis 157 of the elongated member 153.

In some embodiments, such a surgical device 10 can be percutaneously placed into bone. In certain embodiments, the distal end 152 of the elongated member 153 can be configured to displace cancellous bone within the bone. The bone may comprise a vertebral body. In certain embodiments, such a surgical device 10 can be percutaneously placed into an intervertebral disc.

In some embodiments, the elongated member 153 can include a rigid shaft and a moveable distal tip portion 166. The handle 160 can include an actuating member coupled to and configured to move the distal tip portion. The actuating member may comprise the lever 162 adapted to be displaced relative to the handle 160. Displacement of the lever 162 relative to the handle 160 may move the distal tip portion 166 of the elongated member 153. In certain embodiments, the distal tip portion 166 of the elongated member 153 can be configured to scrape bone. For example, the distal tip portion 166 of the elongated member 153 may be adapted to rotate axially relative to the rigid shaft. In such an embodiment, the distal tip portion 166 may be rotated axially to scrape bone.

In some embodiments, such a surgical device 10 can further include an axial load limiting mechanism 186 coupled to the handle 160 and to the elongated member 153.

In some embodiments of a method of the present invention, an elongated member 153 having a shaft can be inserted into a patient's body, and at least a distal portion 166 of the elongated member 153 can be placed into a bone in the patient's body. For example, at least the distal portion 166 of the elongated member 153 may be placed into a vertebral body. In such embodiments, the distal portion 166 of the elongated member 153 may be moved relative to the shaft. A first torque force can be applied to the handle 160 coupled to the elongated member 153 so as to rotate the shaft of the elongated member 153 axially about a longitudinal axis 157 of the shaft. A second torque force can be applied to the handle 160 that exceeds a predetermined amount of torque so as to disengage the handle 160 from the shaft and rotate the handle 160 without rotating the shaft of the elongated member 153. Such an embodiment can further include rotating the handle 160 to re-engage the handle 160 with the shaft, and applying the first torque force on the handle 160 to rotate the shaft.

In certain embodiments of such a method, the lever 162 coupled to the distal portion 166 of the elongated member 153 may be actuated to move the distal portion 166 of the elongated member 153. Moving the distal portion 166 of the elongated member 153 may further include rotating the distal portion 166 axially relative to the shaft. Moving the distal portion 166 of the elongated member 153 may further include displacing cancellous bone within the bone and/or scraping bone.

In some embodiments, such a method may further include limiting an axial load placed on the distal portion 166 of the elongated member 153.

In some embodiments of the present invention, the surgical device 10 can include the handle 160 and the elongated member 153 configured to releasably extend from the handle 160 such that the distal end 152 of the elongated member 153 can be percutaneously placed into a tissue in a patient's body. Such an embodiment can further include a plurality of the elongated members 153, each elongated member 153 having a different configuration and removably attachable to the handle 160. In certain embodiments, the device 10 can further include a docking mechanism 280 secured to the handle 160 for docking the elongated member 153 to the handle 160. In certain embodiments, the device 10 can further include a coupler mechanism 300 adapted to releasably secure the elongated member 153 to the handle 160. In particular embodiments, the distal end 166 of the elongated member 153 can be configured to scrape bone.

In some embodiments of a method of the present invention, a first elongated member 153 having an operable distal portion 166 and releasably extending from the handle 160 can be inserted percutaneously into a tissue in a patient's body. At least the distal portion 166 of the first elongated member 153 can be placed into the tissue, and the distal portion 166 operated in the tissue. Then, the first elongated member 153 can be removed from the tissue, and removed from the handle 160. Next, a second elongated member 153 having an operable distal portion 166 can be releasably attached to the handle 160, and at least the distal portion 166 of the second elongated member 153 can be inserted percutaneously into the tissue. The distal portion 166 of the second elongated member 153 can then be operated in the tissue.

In such a method, the handle 160 can further include the lever 162 adapted to be coupled to the distal portions 166 of the first and second elongated members 153. The distal portions 166 of the first and the second elongated members 153 may be operated in the tissue by actuating the lever 162. Operating the distal portions 166 of the first and the second elongated members 153 in the tissue may further include rotating the distal portions 166 axially. Operating the distal portions 166 of the first and the second elongated members 153 in the tissue may further include displacing a cancellous bone within a bone and/or scraping bone.

In some embodiments of the present invention, the surgical device 10 can include the handle 160 and the elongated member 153 extending from the handle 160. The elongated member 153 can be configured such that the distal portion 166 of the elongated member 153 can be percutaneously placed into a tissue in a patient's body. The surgical device 10 can include an axial load limiting mechanism 186 coupling the elongated member 153 to the handle 160. In certain embodiments, the elongated member 153 may further include a rigid shaft and a moveable distal portion 166, and the handle 160 can further include an actuating member coupled to and configured to move the moveable distal portion 166. In one such embodiment, the actuating member may further comprise the lever 162 adapted to be displaced relative to the handle 160. Displacement of the lever 162 can move the moveable distal portion 166 of the elongated member 153.

In certain embodiments, the distal portion 166 of the elongated member 153 can be configured to displace a cancellous bone within a bone. In certain embodiments, the device 10 can be adapted to operate in a vertebral body and/or in an intervertebral disc. In certain embodiments, the distal portion 166 of the elongated member 153 can be configured to scrape bone.

In some embodiments of a method of the present invention, the distal portion 166 of the elongated member 153 can be inserted percutaneously into tissue in a patient's body, and a force can be applied to the handle 160 coupled to the elongated member 153. In this way, an axial load can be generated along a length of the elongated member 153. At least a portion of the axial load can be released once the axial load exceeds a predetermined level. In certain embodiments, the lever 162 coupled to the distal portion 166 of the elongated member 153 can be actuated to move the distal portion 166 of the elongated member 153. The distal portion 166 of the elongated member 153 can be configured to displace a cancellous bone within the bone and/or scrape bone.

Some embodiments of the present invention can include a torque limiting mechanism 170 and interchangeable elongate members 153, or shafts, having operable distal portions, such as surgical implements 166. Some embodiments of the present invention can include an axial load limiting mechanism 186 and interchangeable elongate members 153, or shafts, having operable distal portions, such as surgical implements 166. Some embodiments of the present invention can include a torque limiting mechanism 170, an axial load limiting mechanism 186, and interchangeable elongate members 153, or shafts, having operable distal portions, such as surgical implements 166. Some embodiments of the present invention can include any combination of a torque limiting mechanism 170, an axial load limiting mechanism 186, and interchangeable elongate members 153 with an actuating member, such as the lever 162, operably connected to these components.

Although the present invention has been described with reference to particular embodiments, it should be recognized that these embodiments are merely illustrative of the principles of the present invention. Those of ordinary skill in the art will appreciate that a torque limiting device and methods of the present invention may be constructed and implemented in other ways and embodiments. Accordingly, the description herein should not be read as limiting the present invention, as other embodiments also fall within the scope of the present invention.

What is claimed is:

1. A surgical device comprising:
a handle having a lever pivotably connected thereto;
a docking assembly secured to the handle and having a docking rod operably attached to the lever and axially slidable within the docking assembly;
a shaft assembly comprising a shaft rod axially slidable within a detachable shaft and removably attachable to the docking rod;
a coupler assembly adapted to releasably secure the shaft assembly to the docking assembly; and
a surgical implement attached to a distal end of the shaft rod operable with the lever.

2. The device of claim 1, further comprising internal threads in a distal end of the docking rod, and external threads on the proximal end of the shaft rod adapted to matingly thread into and out of the internal threads in the docking rod.

3. The device of claim 1, the docking assembly further comprising a docking assembly housing and a projection extending at a substantially 90 degree angle from the docking rod and in contact with the docking assembly housing so as to prevent the docking rod from rotating within the docking assembly housing.

4. The device of claim 1, further comprising external threads on a distal end of the docking assembly, and the coupler assembly further comprising a coupler cap having internal threads adapted to matingly thread onto and off of the external threads of the docking assembly.

5. The device of claim 4, wherein the coupler assembly further comprises a cap retention mechanism adapted to maintain the coupler cap about the coupler assembly sleeve.

6. The device of claim 4, further comprising external threads on a distal end of the docking assembly, the external threads having a thread notch, the shaft shoulder further comprising a shoulder flat, and the coupler assembly further comprising a thread key extending from a proximal end of the coupler assembly sleeve, wherein the thread key is alignable with the shoulder shaft and insertable into the thread notch so as to orient the surgical implement relative to the handle and prevent the shaft assembly and surgical implement from rotating.

7. The device of claim 1, wherein the shaft assembly further comprises a shaft shoulder attached to a proximal end of the detachable shaft and adapted to abut against a distal surface of the docking assembly, and wherein the coupler assembly further comprises a sleeve fixedly attachable about the proximal end of the detachable shaft and a coupler cap axially slidable about the sleeve over the shaft shoulder and onto the docking assembly and adapted to secure the shaft assembly to the docking assembly.

8. The device of claim 1, further comprising a plurality of shaft assemblies, each shaft assembly having a different configuration and removably attachable to the docking assembly.

9. The device of claim 1, wherein the surgical implement comprises a curette tip.

* * * * *

UNITED STATES PATENT AND TRADEMARK OFFICE
CERTIFICATE OF CORRECTION

| | | |
|---|---|---|
| PATENT NO. | : 8,021,365 B2 | Page 1 of 1 |
| APPLICATION NO. | : 11/731364 | |
| DATED | : September 20, 2011 | |
| INVENTOR(S) | : Phan | |

It is certified that error appears in the above-identified patent and that said Letters Patent is hereby corrected as shown below:

On Title Page 2, in Item (56), under "OTHER PUBLICATIONS", in Column 2, Line 21, delete "Mimimal" and insert -- Minimal --, therefor.

In Fig. 19, Drawing Sheet 14 of 20, for Tag "268", in Line 1, delete "tongue" and insert -- torque --, therefor.

Figure 29:
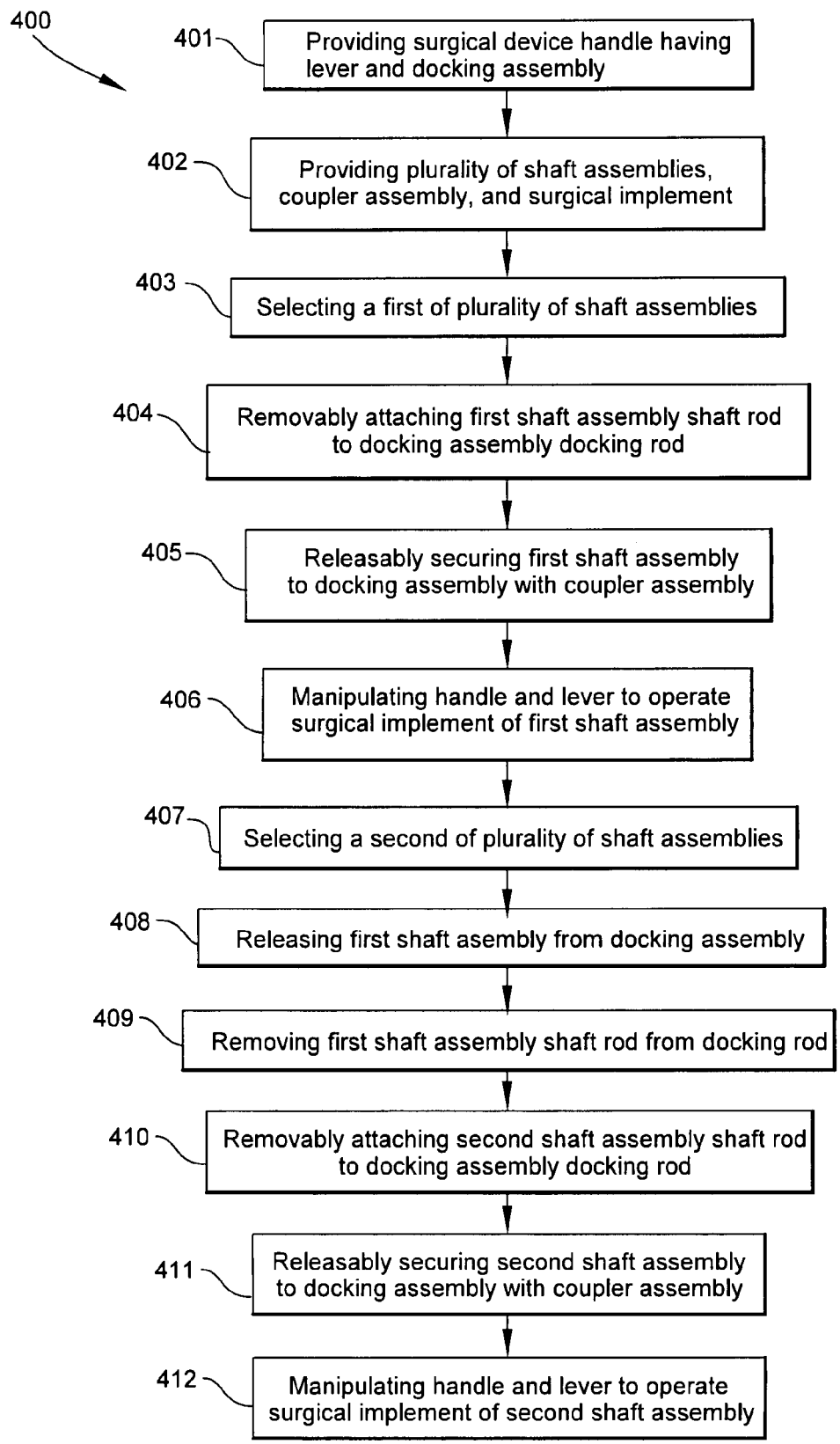
FIG. 29 is a block diagram representation of an embodiment of a method of the present invention.

In Fig. 29, Drawing Sheet 20 of 20, for Tag "408", in Line 1, delete "asembly" and insert -- assembly --, therefor.

In Column 27, Line 23, in Claim 3, delete "claim 1," and insert -- claim 1, wherein --, therefor.

Signed and Sealed this
Third Day of January, 2012

David J. Kappos
*Director of the United States Patent and Trademark Office*